US009200256B2

(12) United States Patent
Sciorra

(10) Patent No.: US 9,200,256 B2
(45) Date of Patent: Dec. 1, 2015

(54) MULTIPOTENT STEM CELL CULTURES

(75) Inventor: Leonard Sciorra, Neshanic Station, NJ (US)

(73) Assignee: Saint Peter's College, Jersey City, NJ (US)

( * ) Notice: Subject to any disclaimer, the term of this patent is extended or adjusted under 35 U.S.C. 154(b) by 431 days.

(21) Appl. No.: 12/992,369

(22) PCT Filed: May 11, 2009

(86) PCT No.: PCT/US2009/043426
§ 371 (c)(1),
(2), (4) Date: Jul. 11, 2011

(87) PCT Pub. No.: WO2009/151844
PCT Pub. Date: Dec. 17, 2009

(65) Prior Publication Data
US 2013/0108588 A1 May 2, 2013

Related U.S. Application Data

(60) Provisional application No. 61/071,682, filed on May 12, 2008, provisional application No. 61/052,478, filed on May 12, 2008.

(51) Int. Cl.
| | |
|---|---|
| *C12N 5/071* | (2010.01) |
| *C12N 5/073* | (2010.01) |
| *C12N 5/074* | (2010.01) |
| *C12N 5/077* | (2010.01) |
| *C12N 5/0775* | (2010.01) |

(52) U.S. Cl.
CPC ............ *C12N 5/0662* (2013.01); *C12N 5/0605* (2013.01); *C12N 5/0607* (2013.01); *C12N 2502/02* (2013.01); *C12N 2506/1307* (2013.01)

(58) Field of Classification Search
None
See application file for complete search history.

(56) References Cited

U.S. PATENT DOCUMENTS

| 8,021,876 B2 * | 9/2011 | Atala et al. ................. 435/325 |
| 2004/0071749 A1 | 4/2004 | Dobson |
| 2005/0124003 A1 | 6/2005 | Atala |
| 2007/0059293 A1 | 3/2007 | Atala |

OTHER PUBLICATIONS

Hovatta, Outi; et al; "A culture system using human foreskin fibroblasts as feeder cells allows production of human embryonic stem cells" Human Reproduction, 18, 1404-1409, 2003.*
Lagasse, Eric; et al; "Purified hematopoietic stem cells can differentiate into hepatocytes in vivo" Nature Medicine, 6, 1229-1234, 2000.*
Chang C Medium Data Sheet, Irvine Scientific.*
Wanders, RJA; et al; "Mitochondrial Oxidative Phosphorylation in Digitonin-permeabilized Chorionic Villus Fibroblasts: A New Method with Potential for Prenatal Diagnosis" Journal of Inherited Metabolic Disorders, 17, 304-306, 1994.*
van den Engh, GJ; et al; "Preparation and Bivariate Analysis of Suspensions of Human Chromosomes" Cytometry, 6, 92-100, 1985.*
Fauza, Dario; "Amniotic fluid and placental stem cells" Best Practice & Research Clinical Obstetrics and Gynaecology, 18, 877-891, 2004.*
Kang, HY; et al; "The dermal stem cell factor and c-kit are overexpressed in melasma" Clinical and Laboratory Investigations, 154, 1094-1099, 2006.*
Bartsch, Georg Jr; et al; "Propagation, Expansion, and Multilineage Differentiation of Human Somatic Stem Cells from Dermal Progenitors" Stem Cells and Development, 14, 337-348, 2005.*
Toma Jean G; et al; "Isolation and Characterization of Multipotent Skin-Derived Precursors from Human Skin" Stem Cells, 23, 727-737, 2005.*
Medina, Reinhold J; et al; "Isolation of Epithelial Stem Cells From Dermis by a Three-Dimensional Culture System" Journal of Cellular Biochemistry, 98, 174-184, 2006.*
Chang H-C, "Human amniotic fluid cells grown in a hormone-supplemented medium: suitability for prenatal diagnosis," *Proceedings of the National Academy of Sciences* 79(15)4795-4799 (1982).
Chang, H-C and Jones, O.W., "Reduction of sera requirement sin amniotic fluid cell culture," *Prenatal Diagnosis* 5(5):305-312 (1985).
Crigler, L et al., "Isolation of mesenchymal cell population from murine dermis that contains progenitors of multiple cell lineages," *FASEB Journal* 21(9):2050-2063 (2007).
Coghlan, A., "Woman receives windpipe built from her stem cells," *NewScientist* (2008), available on the Internet at URL (http://www.newscientist.com/article/dn16072-woman-receives-windpipe-built-from-her-stem-cells html).
De Coppi, P.D., et al , "Isolation of amniotic stem cell lines with potential for therapy," *Nature Biotechnology* 25(1):100-106 (2007).
Gever, J., "Pluripotent Stem Cells Created from Adult Cells Without Gene Transfer," *MedPage Today* (2009).
GIBCO, "Amniomax product information," (2003) available on the internet at URL (http://tools.invitrogen.com/content/sfs/manuals/3958%20Amniomax.pdf).

(Continued)

*Primary Examiner* — Blaine Lankford
*Assistant Examiner* — David Berke-Schlessel
(74) *Attorney, Agent, or Firm* — Proskauer Rose LLP

(57) ABSTRACT

The invention provides methods for propagation of multipotent stem cells from human skin fibroblast samples using an appropriate medium, such as an amniotic fluid medium (AFM), and subsequent differentiation of the cells into cells of any of the three germ layers. The invention also provides methods of differentiating and making various tissues from multipotent cells in skin fibroblasts cultures that are capable of in vitro differentiation and that the cells are useful as a source of in vivo gene and/or autologous cell therapy. Isolated multipotent stem cells, cultures of multipotent stem cells, and differentiated cells derived from the cultures of multipotent stem cells that are obtained by the methods disclosed herein also are provided. The methods, cells, cultures, media, banks, batches, and collections so provided can be used for various medical, research, diagnostic and therapeutic uses.

9 Claims, 5 Drawing Sheets

(56) References Cited

OTHER PUBLICATIONS

International Search Report for International Patent Application No. PCT/US2009/0043426 (2009).

Iparraguirre, S. et al., "Nerve-like Cells Obtained From Frozen Human Fibroblasts Grown in DMSO-Free Nerve Differentiation Media," *49th Meeting of the American Society of Cell Biology* (poster) (San Diego, CA, 2009).

Kim, J. et al., "Human amniotic fluid-derived stem cells have characteristics of mulitpotent stem cells," *Cell Proliferation* 40(1):75-90 (2007).

Lysy, P A. et al , "Human skin fibroblasts From mesodermal to hepatocyte-like differentiation," *Hepatology* 46(5) 1574-1585 (2007).

Miettienen, M. and Lasota, J , "KIT (CD117) A Review on Expression in Normal and Neoplastic Tissues, and Mutations and Their Clinicopathologic Correlation," *Applied Immunochemistry & Molecular Morphology* 13(3):205-220 (2005).

Motluk, A., "Stem cells from menstrual blood save limbs," *NewScientist* (2008) available on the internet at URL (http://www.newscientist com/article/dn14559-stem-cells-from-menstrual-blood-save-limbs html).

Motohashi, T , et al., "Unexpected multipotency of melanoblasts isolated from murine skin," *Stem Cells* 27(4):888-897 (2009).

Murphy, M.P., et al., "Allogeneic endometrial regenerative cells• An "Off the shelf solution" for critical limb ischemia?" *Journal of Translational Medicine* 6(45):1-8 (2008).

Park, I-H et al., "Reprogramming of human somatic cells to pluripotency with defined factors," *Nature* 451(7175).141-146 (2008).

Sciorra, L J. et al., "Patient variability in neurogenic cell differentiation of human amniotic fluid multipotent stem cells," *47th Meeting of the American Society of Cell Biology* (poster) (Wasington, DC, 2007).

Sciorra, L J et al., "Frozen human fibroblasts of varying ages contain numerous multipotent cells capable of in vitro differentiation into cells of all three germ layers," *Annual Meeting of Developmental Biology*, ISSN 0121606, vol. 139, No. 2, p. 553 (poster) (Philadelphia, PA, 2008).

Shrestha, R. et al., "An in Vitro Time Course Study Using Expression Microarray Analysis on Differentiated Nerve-Like Cells Originating From Frozen Human Fibroblasts," *European Molecular Biology Organization (EMBO) Meeting*, p. 165 (poster) (Barcelona, Spain, 2010).

Stevens, A.M, et al., "Liver biopsies from human females contain male hepatocytes in the absence of transplantation," *Laboratory Investigation* 84(12)•1603-1609 (2004).

Takahashi, K et al., "Induction of Pluripotent Stern Cells from Adult Fibroblasts by Defined Factors," *Cell* 131:861-872 (2007).

Warren, L, et al , "Highly Efficient Reprogramming to Pluripotency and Directed Differentiation of Human Cells with Synthetic Modified mRNA," *Cell Stem Cell* 7:1-13 (2010).

Written Opinion of the International Searching Authority for International Patent Application No. PCT/US2009/0043426 (2009).

Yu, J et al., "Induced Pluripotent Stem Cell Lines Derived from Human Somatic Cells," *Science* 318(5858):1917-1920 (2007).

Zhou, H. et al , "Generation of Induced Pluripotent Stem Cells Using Recombinant Proteins," *Cell Stern Cell* 4:1-4 (2009).

Priest, Jean H., "Prenatal Chromosomal Diagnosis and Cell Culture", The Act Cytogenetics Laboratory Manual, Second Edition, 1991, p. 149-168, Published by Raven Press, Ltd., New York.

Barch, M., The Act Cytogenetics Laboratory Manual, Second edition, 1991. Chapter 5, p. 155.

\* cited by examiner

MULTIPOTENT STEM CELL CULTURES

This application claims priority to U.S. provisional application Ser. No. 61/052,478, filed May 12, 2008, and U.S. provisional application Ser. No. 61/071,682, filed May 12, 2008, the entireties of which are hereby incorporated by reference.

FIELD OF THE INVENTION

The invention relates to and provides for methods for propagation of multipotent stem cells from human skin fibroblast samples using appropriate culture media, such as amniotic fluid media, and differentiation of the multipotent stem cells so obtained into any of the three germ layers, as desired, and cultures and banks of multipotent stem cells, multipotent stem cells, and uses of all of the above.

BACKGROUND OF THE INVENTION

Recently, studies have shown that human skin fibroblasts can be reprogrammed into induced pluripotent stem (iPS) cells via transduction of four viral genes (Takahashi, et al. (2007). *Cell.* 131: 861-872; Yu, et al. *Science.* 318 (5858): 1917-1920; Park, et al. *Nature.* 451: 141-146). These iPS cells have stem cell characteristics and can differentiate into cells of all three germ layers, a property known as pluripotency. The pluripotency concept has met skepticism regarding the abilities and potential dangers of these cells, however. Thus, the therapeutic uses of patient-specific iPS cells will be met with caution, as genetic alterations due to retroviral introduction must be investigated.

Creation of pluripotent stem cells from adult mouse cells without gene transfer has recently been reported in *MedPage Today* (John Gever, Edited, Published: Apr. 24, 2009.). The report based on Zhou H, et al.'s investigation demonstrate adult mouse cells can be reprogrammed into pluripotent stem cells with recombinant transcript factor proteins instead of genes (see Zhou H, et al. "Generation of induced pluripotent stem cells using recombinant proteins" *Cell Stem Cell* 2009; DOI: 10.1016/j.stem.2009.04.005). The transformed cells were able to form embryoid bodies and to differentiate into cells characteristic of the three primary germ layers: endoderm, mesoderm, and ectoderm.

A study by De Coppi et al. (*Nat Biotechnol.* 25(1):100-106 (2007) has shown that amniotic fluid cultures harbor multipotent stem cells that are not tumorigenic in mice. The researchers also found that amniotic fluid cultures initially show low levels (1%) of multipotent cells (CD117$^+$ cells), a stem cell marker. After isolating such cells with microbeads, they were capable of differentiating into cells of any of the three germ layers.

De Coppi et al. isolated human and rodent amniotic fluid-derived stem (AFS) cells that express stem cell markers using immunoselection with magnetic microspheres from human amniocentesis specimens. AFS cells were grown in α-Minimum Essential Medium (α-MEM) containing 15% ES-FBS, 1% glutamine and 1% penicillin/streptomycin (Gibco), supplemented with 18% Chang B and 2% Chang C media (Irvine Scientific) at 37° C. with 5% $CO_2$. Chang's media as supplemented in AFS cell cultures has been known for reduction of sera requirements in amniotic fluid cell culture. Chang and Jones reported (*Prenat Diagn.* 1985 September-October; 5(5):305-12) that addition of 10 growth promoting factors reduce serum requirement in the medium and the supplemented medium preserved the cells. However, it is not known if the supplemental growth factors preserved the cells for repeated passages.

In an earlier publication, Chang et al. (*Proc Natl Acad Sci USA,* 1982 August; 79(15):4795-9) also reported stability of human amniotic fluid cells grown in a hormone-supplemented medium. Chang et al. described development of a new supplemented medium to improve human amniotic fluid cell growth and to reduce the dependence on exogenously added serum. The Chang's medium includes a mixture of Ham's F12 medium and Dulbecco's modified Eagle's medium supplemented with Hepes, antibiotics, and 10 growth-promoting factors at 4% fetal bovine serum (see Chang et al. Table 1). Chang media compositions (CHANG MEDIUM®, Irvine Scientific), show Chang C medium formula contains an amount of Steroid Hormones. However, it is not known if the growth factors in the CHANG MEDIUM® play any role in the propagation of multipotent cells in amniotic fluid media.

Kim et al. (*Cell Prolif.* 40: 75-90 (2007)) reported isolation of fibroblastoid-type cells from human amniotic fluid (HAF) and subculture in culture medium containing Dulbecco's modified Eagle's medium (DMEM) (Gibco, Grand Island, N.Y.) supplemented with 100 U/ml penicillin, 0.1 mg/ml streptomycin (Gibco), 3.7 mg/ml sodium bicarbonate, 10 ng/ml epidermal growth factor (EGF) (Peprotech, Princeton, N.J.) 10% fetal bovine serum (FBS) (Gibco). Seven days after the initiation of the culture, the medium was replaced with fresh ones, and subsequently replaced twice a week. The HAF-derived fibroblastoid-type cells that were passaged 8 times contained stem cells and were used for differentiation experiments Crigler et al. (*FASEB J.* 21(9): 2050-2063 (2007)) demonstrated the presence of low numbers of multipotent cells (CD117$^+$ cells) in the murine dermis and suggested that the cells can be repeatedly isolated from neonatal murine dermis by a sequence of differential centrifugation and be used for epidermal differentiation.

Recently Motohashi et al. reported that melanoblasts cells isolated from murine skin have multipotency and self-renewal capabilities. Isolated melanoblasts cells from mice skin were differentiated into neurons, glial cells, smooth muscle cells and melanocytes. Differentiation of the cells was inhibited by antagonist ACK2 (*Stem Cells*. April 2009, 27(4):888-97).

Stem cells harvested from a woman's bone marrow has been used to populate a stripped-down section of windpipe received from a donor and successfully transplanted into the woman's body (see *NewScientist*, "Woman receives windpipe built from her stem cells", Nov. 19, 2008 by Andy Coghlan.

Stem cells derived from human menstrual blood have has been reported to prevent limbs with restricted blood flow from withering in mice (see *NewScientist*, "Stem cells from menstrual blood save limbs", Aug. 19, 2008 by Alison Motluk. Investigators also believe that cells coming out of menstrual blood are regenerative (see Murphy et al., *Journal of Translational Medicine,* 6:45, Aug. 19, 2008).

Stevens et al. (see Stevens et al. *Lab Invest.* December; 84(12):1603-9, 2004) reported that fetal cells developed during pregnancy can persist in the mother's blood and tissues for decades. Studies have found that circulating stem cells can lead to liver regeneration with donor-derived hepatocytes. More specifically, male cells were found in livers of mothers who carried male babies, and these cells expressed hepatocyte antigens. This study provides a natural basis for regeneration of an organ from stem cells. Stevens et al. did not address if multipotent stem cells in human skin fibroblast samples can be propagated, differentiated and be used for regeneration of a desired organ, however. Rather, Stevens merely documented a natural phenomenon.

Umbilical cord blood is known to contain stem cells, and cord blood banks have been established.

There remains a need, however, to provide approaches for obtaining stem cells of both sexes without the need for recombinant gene or protein transfer in order to permit autologous therapy.

The present invention, provides for the first time methods for propagating, without the need for an initial isolation, multipotent stem cells from human skin fibroblast samples of both sexes of all races (including African-American and Caucasian female and male sources), using an appropriate medium, such as an amniotic fluid medium (AFM) and other media and various growth factors disclosed herein, and subsequent differentiation into cells of any of the three germ layers. It was surprising and unexpected that a rare cell type like a multipotent cell could be grown without first isolating because it was thought that other cell types, including non-potent fibroblasts, would overwhelm the rare cells types in culturing, particularly during multiple passages. The methods disclosed herein also allow for enhanced production of such multipotent stem cells without the need for gene or viral transduction of cell. Due to the efficiency of the disclosed methods, stem cells from an individual can be obtained and propagated to allow for autologous or otherwise type matched stem cell therapies, including tissue and organ grafts and supplementation, tissue and organ regeneration, and tissue and organ replacement. Prior to the present invention, such was simply not practical for the general public in a therapeutic setting. The invention also provides model systems to assess gene pathways in vitro and their effects in and during cell differentiation.

SUMMARY OF THE INVENTION

The present invention relates generally to methods for propagation of multipotent stem cells from human skin fibroblast samples using an appropriate medium, such as an amniotic fluid medium (AFM) and other media, including various growth factors, and allows for differentiation of the multipotent stem cells into cells of any of the three germ layers.

The invention also provides isolated multipotent stem cells, cultures of multipotent stem cells, and the differentiated cells derived from the cultures of multipotent stem cells that are obtained by the methods disclosed herein.

In one embodiment, the invention provides methods for propagation of multipotent stem cells in human skin fibroblast cultures comprising the steps of: a) propagating cells of a human skin fibroblast sample using an appropriate culture medium, such as an amniotic fluid medium (AFM); b) allowing the cells to propagate for multiple (more than one, preferably at least three) passages in the AFM; c) determining the number of CD117+ stem cells in the culture; and d) prolonging the human skin fibroblast culture by continued passages in the AFM until a high number of CD117+ stem cells is attained.

In another embodiment, the invention provides above described methods, which are further comprising differentiating the propagated $CD117^+$ multipotent stem cells into cells of any of the three germ layers. The $CD117^+$ multipotent stem cells can be differentiated into adipose, hepatic, muscle, and nerve tissues, as desired.

In another embodiment, the invention provides isolated multipotent stem cells obtained from human skin fibroblast samples, wherein the culture is propagated by a method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; c) determining the number of $CD117^+$ multipotent stem cells in the culture; and d) prolonging the human skin fibroblast culture by continued passages in the AFM until a high number of $CD117^+$ multipotent stem cells is attained.

In another embodiment, the invention provides methods for propagation of multipotent stem cells in human skin fibroblast samples, wherein the method comprising the steps of: a) propagating cells of a human skin fibroblast sample in an appropriate culture medium, such as an amniotic fluid growth medium (AFM); and b) allowing the cells to propagate for multiple (more than one, preferably at least three) passages in the AFM. The number of $CD117^+$ multipotent stem cells in the culture can be determined after each passage. In another embodiment, the human skin fibroblast culture is prolonged by continued passages in the AFM until a high number of CD117+ stem cells is attained.

In another embodiment, the propagated $CD117^+$ multipotent stem cells can be differentiated into cells of any of the three germ layers. The $CD117^+$ multipotent stem cells can be differentiated into adipose, hepatic, muscle, and nerve tissues, for example.

In another embodiment, the invention provides isolated multipotent stem cells obtained from human skin fibroblasts culture, wherein the culture is propagated by a method comprising the steps of: a) propagating cells of a human skin fibroblast sample in an appropriate culture medium, such as an amniotic fluid growth medium (AFM); and b) allowing the cells to propagate for multiple (more than one, preferably at least three) passages in the AFM. The number of $CD117^+$ multipotent stem cells in the culture can be determined after each passage, if desired. The human skin fibroblast culture can be prolonged by continued passages in the AFM until a high number of CD117+ stem cells is attained.

In another embodiment, the invention provides isolated multipotent stem cells obtained from human skin fibroblasts culture, wherein the culture is propagated by a method comprising the steps of: a) propagating cells of a human skin fibroblast sample in an appropriate culture medium, such as an amniotic fluid growth medium (AFM); and b) allowing the cells to propagate for multiple (more than one, preferably at least three) passages in the AFM. The propagated $CD117^+$ multipotent stem cells can be differentiated into cells of any of the three germ layers. The $CD117^+$ multipotent stem cells can be differentiated into adipose, hepatic, muscle, and nerve tissues, and allow for autologous grafts, regeneration, and replacement.

In another embodiment, the invention provides methods for differentiation of multipotent cells from human skin fibroblasts culture into cells of germ layers, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated $CD117^+$ multipotent stem cells into cells of a desired germ layer under suitable conditions, and allow for autologous grafts, regeneration, and replacement.

In another embodiment, the invention provides methods of making adipose tissues from multipotent cells in human skin fibroblasts culture, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into cells of the germ layer; wherein the method provides adipose tissues under suitable conditions, and allow for autologous grafts, regeneration, and replacement.

In another embodiment, the invention provides methods of making hepatic tissues from multipotent cells in human skin fibroblasts culture, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into a cell of the germ layer; wherein the method provides hepatic tissues under suitable conditions, and allow for autologous grafts, regeneration, and replacement.

In another embodiment, the invention provides methods of making muscle tissues from multipotent cells in human skin fibroblasts culture, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into a cell of the germ layer; wherein the method provides muscle tissues under suitable conditions, and allow for autologous grafts, regeneration, and replacement.

In another embodiment, the invention provides methods of making nerve tissues from multipotent cells in human skin fibroblasts culture, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into a cell of the germ layer; wherein the method provides nerve tissues under suitable conditions, and allow for autologous grafts, regeneration, and replacement.

In another embodiment, the invention provides cultures of multipotent stem cell obtained from human skin fibroblasts culture, wherein the culture is propagated by a method comprising the steps of: a) propagating cells of a human skin fibroblast sample in an appropriate culture medium, such as an amniotic fluid growth medium (AFM); and b) allowing the cells to propagate for multiple (more than one, preferably at least three) passages in the AFM.

In another embodiment, the invention provides collections of differentiated cells derived from a culture of a multipotent stem cells of human skin fibroblasts culture, wherein the differentiated cells are obtained by: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into cells of a desired germ layer under suitable conditions, and allow for autologous grafts, regeneration, and replacement.

In another embodiment, the invention provides collections of differentiated adipose cells derived from a culture of a multipotent stem cells of human skin fibroblasts culture, wherein the differentiated cells are obtained by: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into adipose cells under suitable conditions, and allow for autologous grafts, regeneration, and replacement.

In another embodiment, the invention provides collections of differentiated hepatic, cells derived from a culture of a multipotent stem cells of human skin fibroblasts culture, wherein the differentiated cells are obtained by: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into hepatic cells under suitable conditions, and allow for autologous grafts, regeneration, and replacement.

In another embodiment, the invention provides collections of differentiated muscle, cells derived from a culture of a multipotent stem cells of human skin fibroblasts culture, wherein the differentiated cells are obtained by: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated CD117$^+$ multipotent stem cells into muscle cells under suitable conditions, and allow for autologous grafts, regeneration, and replacement.

In another embodiment, the invention provides collections of differentiated nerve tissues derived from a culture of a multipotent stem cells of human skin fibroblasts culture, wherein the differentiated cells are obtained by: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated CD117$^+$ multipotent stem cells into nerve tissues under suitable conditions, and allow for autologous grafts, regeneration, and replacement.

In another embodiment, the invention provides methods for repairing a liver in a patient in need using CD117+ multipotent stem cells, wherein the method comprises: (I) making liver tissue by differentiating CD117+ multipotent cells, wherein the CD117+ cells are produced by a method comprising the steps of: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated CD117$^+$ multipotent stem cells into cells of a germ layer; wherein the method provides liver tissue under suitable conditions; and (II) treating the patient with the liver tissue obtained from (I). According to another embodiment, the cells at step (b) are cryo-preserved prior to step (c).

In another embodiment, the invention provides methods for repairing a lung in a patient in need using CD117+ multipotent stem cells, wherein the method comprises: (I) making lung tissue by differentiating CD117+ multipotent cells, wherein the CD117+ cells are produced by a method comprising the steps of: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated CD117$^+$ multipotent stem cells into cells of a germ layer; wherein the method provides lung tissue under suitable conditions; and (II) treating the patient with the lung tissue obtained from (I). According to another embodiment, the cells at step (b) are cryo-preserved prior to step (c).

In another embodiment, the invention provides methods for repairing a kidney in a patient in need using CD117+ multipotent stem cells, wherein the method comprises: (I) making kidney tissue by differentiating CD117+ multipotent cells, wherein the CD117+ cells are produced by a method comprising the steps of: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated $CD117^+$ multipotent stem cells into cells of a germ layer; wherein the method provides kidney tissue under suitable conditions; and (II) treating the patient with the kidney tissue obtained from (I). According to another embodiment, the cells at step (b) are cryo-preserved prior to step (c).

In another embodiment, the invention provides methods for repairing a pancreas in a patient in need using CD117+ multipotent stem cells, wherein the method comprises: (I) making pancreas tissue by differentiating CD117+ multipotent cells, wherein the CD117+ cells are produced by a method comprising the steps of: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated $CD117^+$ multipotent stem cells into cells of a germ layer; wherein the method provides pancreas tissue under suitable conditions; and (II) treating the patient with the pancreas tissue obtained from (I). According to another embodiment, the cells at step (b) are cryo-preserved prior to step (c).

In another embodiment, the invention provides methods for repairing a heart in a patient in need using CD117+ multipotent stem cells, wherein the method comprises: (I) making heart tissue by differentiating CD117+ multipotent cells, wherein the CD117+ cells are produced by a method comprising the steps of: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated $CD117^+$ multipotent stem cells into cells of a germ layer; wherein the method provides heart tissue under suitable conditions; and (II) treating the patient with the heart tissue obtained from (I). According to another embodiment, the cells at step (b) are cryo-preserved prior to step (c).

In another embodiment, the invention provides methods for repairing or replacing skin in a patient in need using CD117+ multipotent stem cells, wherein the method comprises: (I) making skin tissue by differentiating CD117+ multipotent cells, wherein the CD117+ cells are produced by a method comprising the steps of: a) propagating cells of a human skin fibroblast sample in an suitable culture medium, such as an amniotic fluid growth medium (AFM); b) allowing the cells to propagate for multiple (more than one, preferably at least three) passages in the AFM; and c) differentiating the propagated $CD117^+$ multipotent stem cells into cells of a germ layer; wherein the method provides skin tissue under suitable conditions; and (II) treating the patient with the skin tissue obtained from (I). According to another embodiment, the cells at step (b) are cryo-preserved prior to step (c).

In another embodiment, the invention provides a collection of multipotent stem cells obtained by a method comprising the steps of: a) propagating cells of a human skin fibroblasts sample inoculum in a culture containing amniotic fluid growth medium (AFM) in a container; b) allowing the cells to propagate for multiple (more than one, preferably at least three) passages in the AFM under suitable conditions; and c) collecting the propagated multipotent stem cells having a suitable density, wherein the multipotent stem cells are capable of in vitro differentiation into adipose, hepatic, muscle, or nerve cells.

In another embodiment, the invention provides a collection of differentiated cells derived from a culture of a multipotent stem cells of human skin fibroblasts culture, wherein the differentiated cells are obtained by: a) propagating cells of a human skin fibroblasts sample inoculum in a culture containing amniotic fluid growth medium (AFM) in a container (flask); b) allowing $CD117^+$ multipotent stem cells to propagate for multiple (more than one, preferably at least three) passages in the AFM under suitable conditions; c) differentiating the propagated $CD117^+$ multipotent stem cells into cells of any of the germ layers under suitable conditions; and d) collecting the propagated differentiated cells having a suitable density, wherein the cells are differentiated into adipose, hepatic, muscle, or nerve cells.

In another embodiment, the invention provides a collection of multipotent stem cells having a suitable cell density obtained by propagating a suitable sized inoculum of human skin fibroblasts sample in a culture containing amniotic fluid growth medium (AFM), wherein the multipotent stem cells are capable of in vitro differentiation into adipose, hepatic, muscle, or nerve cells.

In another embodiment, the invention provides a collection of differentiated cells having a suitable cell density derived from a culture of a multipotent stem cells of human skin fibroblasts culture, wherein the differentiated cells are obtained by propagating a suitable sized inoculum of human skin fibroblasts sample in a culture containing amniotic fluid growth medium (AFM) and differentiating the propagated $CD117^+$ multipotent stem cells into cells of any of the germ layers, wherein the cells are differentiated into adipose, hepatic, muscle, or nerve cells.

According one aspect of the invention a suitable size inoculum contains a cell density of about 3,000 to about 5,000 cells/cm$^2$, and a suitable density or the final density of the propagated multipotent stem or differentiated cells is about 50,000 to 10,000,000 cells/cm$^2$ or more.

According another aspect of the invention a suitable size inoculum contains a cell density of about 3,500, 4,000, or 4,500 cells/cm$^2$, and a suitable density or the final density of the propagated multipotent stem or differentiated cells is about 75,000 to about 100,000, about 125,000, about 150,000, about 200,000, about 300,000, about 400,000, about 500,000, about 6,00,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000, or about 10,000,000 cells/cm$^2$ or more.

According to another embodiment, amniotic fluid cells are passaged for about two months or more in AFM.

According to another embodiment, cells of a human skin fibroblast sample are subject to multiple passages, for example, at least 3, 4, 5, 6, 7, 8 or more passages in the AFM.

According to another embodiment, the propagated $CD117^+$ multipotent stem cells are subject to differentiation when the $CD117^+$ cells count reached to a desirable number, for example, at least about 85%.

According to another embodiment, the graft is an organ graft selected from a heart, pancreas, liver, lung, kidney, skin, or other body parts.

According to another embodiment, the CD117+ multipotent stem cells are autologous to the patient.

According to another embodiment, the human skin fibroblast sample is obtained from the patient within one year of the repairing or replacing.

According to another embodiment, the amniotic fluid growth medium (AFM) comprises various growth factors.

The methods, cells, media, cultures, batches, banks, collections, and various growth factors, so provided can be used for various medical, research, diagnostic and therapeutic uses.

The methods according to the invention also can be used as model systems to assess gene pathways in vitro and their affects in and during cell differentiation.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, advantages, and aspects of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

DETAILED DESCRIPTION OF THE INVENTION

Figure 1:
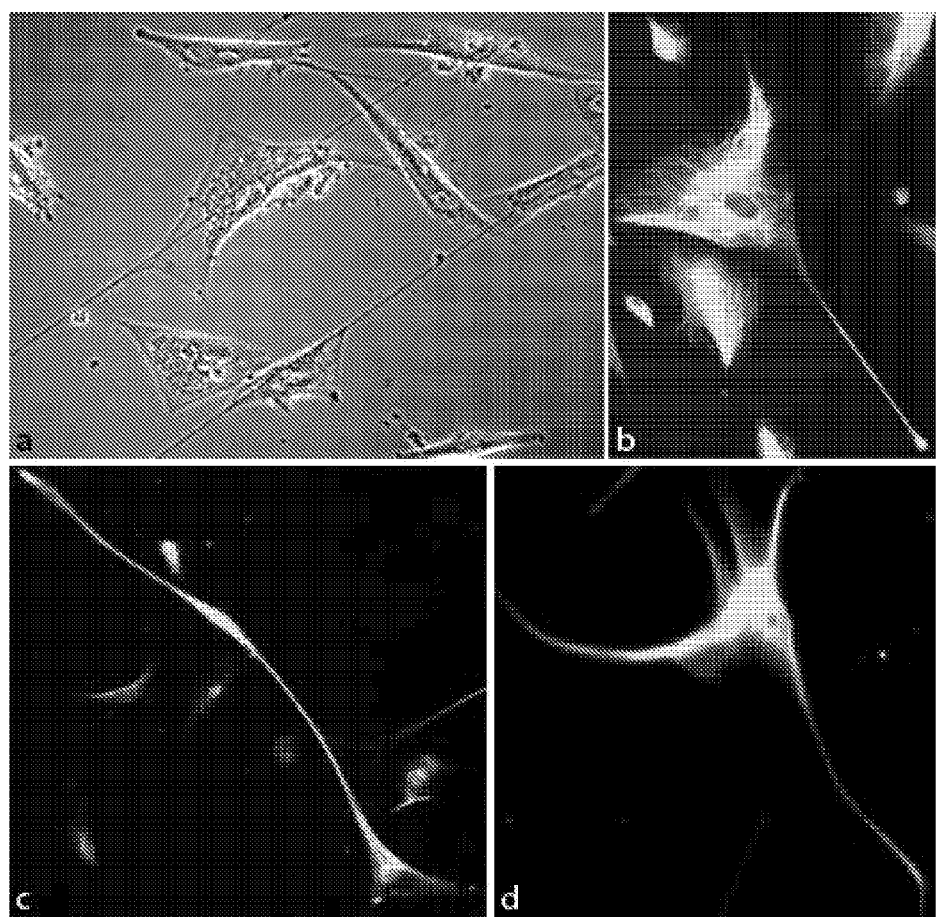
FIG. 1. Representative pictures showing results of adipogenic and nerve differentiation of back-up amniotic fluid samples. a: representative phase contrast picture of adipose cells at 480×; b: representative picture of a pyramidal nerve cell stained with nestin at 480×; c: representative picture of a bipolar nerve cell stained with nestin at 480×; c: representative picture of a multipolar nerve cell stained with nestin at 480×.

The present invention provides here elegant and efficient procedures for obtaining multipotent stems cells without isolation, viral transduction, recombinant gene or protein transfer. The procedures employ culturing conditions for obtaining and propagating stem cells from cell culture and/or tissue samples. Publicly available samples of fibroblast samples from various age groups were obtained from the Coriell Cell Repository (Camden, N.J.). Under suitable culture conditions that are disclosed herein, all these frozen samples yielded large numbers of multipotent cells that could differentiate into cells with a morphologic appearance of cells from any of the three germ lines, specifically, adipogenic, hepatic, myogenic, and neurogenic cells. The invention also provides methods of differentiating and making various tissues from multipotent cells in skin fibroblasts cultures that are capable of in vitro differentiation, isolated multipotent stem cells, cultures of multipotent stem cells, and the differentiated cells derived from the culture multipotent stem cells that are obtained by the methods disclosed herein.

The present invention also provides that multipotent stem cells in human skin fibroblast samples of both sexes of all races can be propagated, differentiated and be used for regeneration, recreation repopulation and/or reconstitution of desired tissues and organs. For example, in one embodiment, the invention provides autologous therapies based on propagated multipotent stem cells for regeneration of tissues, for use as grafts, tissue/organ replacement or supplementation.

In another embodiment, the invention provides methods of making autologous stem cells for use as a graft and their therapeutic use in autoimmune diseases, in treatment of tissue regenerative disorders, and to provide long-lasting immunosuppressive effects on the host to prevent graft rejection by the host immune system.

Another embodiment provides method of making autologous stem cells for grafts from multipotent cells in human skin fibroblasts culture, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated multipotent stem cells into cells of a germ layer; wherein the method provides graft under suitable conditions.

Yet in another embodiment, the invention provides methods of autologous regeneration of grafts from multipotent cells in human skin fibroblasts culture, wherein the method comprising the steps of: a) propagating cells of a human skin fibroblast sample in an appropriate culture medium, such as an amniotic fluid growth medium (AFM); b) allowing the cells to propagate for multiple (more than one, preferably at least three) passages in the AFM; and c) differentiating the propagated multipotent stem cells into cells of a germ layer; wherein the method provides graft under suitable conditions. The graft can be cells of an organ graft selected from a heart, pancreas, liver, lung, kidney, skin, or other body parts. Grafts also can be used for regeneration of the nervous system, including central and peripheral.

According to one embodiment, amniotic fluid cells obtained from three patient samples that were passaged for more than two months, and resulted in high numbers of CD117+ cells. These cells were capable of differentiation into nerve and adipose tissue. Further, prolonged culturing of human skin fibroblast cultures in an appropriate culture medium, such as an amniotic fluid growth medium (AFM) also resulted in high numbers of CD117+ cells. Other appropriate media may be used in accordance with the teachings contained herein. Examples of other media include, Eagle's Minimal Essential Medium (MEM), Dulbecco's Modified Eagle's Medium (DMEM), RPMI 1640, F-12, IMDM, Alpha Medium and McCoy's Medium, and can be modified by the skilled person in accordance with the teachings contained herein.

Amniotic fluid-derived human stem cells differentiate into cells of any of the three germ layers. Instant investigation involved multipotent cells, including cells in frozen human skin fibroblasts of various age groups, were grown under suitable culturing conditions, including conditions as described herein. Normal cells taken from amniotic fluid (passage 7), prenatal cells (passage 10), a 3-day-old (passage 9), an 11-year-old (passage 9), a 37-year-old (passage 10), and a 96-year-old (passage 8) human were obtained from a commercially available source (such as Coriell Cell Repository, Camden, N.J.). The cell lines that were propagated were those exhibiting fibroblast-like morphology after at least one subculture. Fibroblast cell lines may be established by outgrowth of undifferentiated ectodermal cells from a biopsy or identified by a submitter as a fibroblast cell line. Cell morphology of a fibroblast cell line will vary somewhat with the culture conditions and with the age of the culture or the age of the cell line, but generally the fibroblastic morphology is spindle shaped (bipolar) or stellate (multipolar); usually arranged in parallel arrays at confluence in contact-inhibited cultures. These cells are migratory with processes exceeding the nuclear diameter by threefold or more.

The number of passages of the fibroblasts cultures in amniotic fluid, as shown above, were selected, because, an earlier experiment showed that amniotic fluid cells at passage 8 or more are highly positive for the hematopoietic stem cell marker, CD117, and differentiated into nerve and adipose. The repository cultures received in Eagle's Minimum Essential Medium (MEM) with 15% FBS and were transferred into amniotic growth media (AFM) (see De Coppi et al. (2007) containing: α-MEM, Chang B & C, and 15% ES-FBS. Initial CD117+ counts were: amniotic fluid (81%), prenatal cells (79%), 3-day-old (46%), 11-year-old (47%), 37-year-old (23%), and 96-year-old (0.5%). After 3 passages in AFM, all cultures were >85% CD117+. All the cultures were then differentiated into cells having the morphology and staining characteristics of adipose, hepatic, muscle, and nerve cells. Undifferentiated cells from the repository were also >85% positive for the nuclear stem cell marker, NANOG. The above data indicate that fibroblasts cultures contained numerous cells, which were capable of in vitro differentiation. These multipotent cells are therefore useful as a source of in vivo gene and/or autologous cell therapy and also can be used in model systems to study cellular differentiation, for example, the invention as disclosed herein, including the methods, media, cells, cultures, batches, banks, collections, and various growth factors, can be used as model systems to assess gene pathways in vitro and their affects in and during cell differentiation.

The Chang B & C in the above AFM media provides growth factors. In one embodiment, the growth factors are transferrin, 5 µg/ml; selenium, 20 nM; insulin, 10 µg/ml; triiodothyronine, 0.1 nM; glucagon, 1 µg/ml; fibroblast growth factor, 10 ng/ml; hydrocortisone, 1 nM; testosterone, 1 nM; estradiol, 1 nM; and progesterone, 1 nM. In another embodiment, twice the amount of each growth factor was used so that the media contained transferrin, 10 µg/ml; selenium, 40 nM; insulin, 20 µg/ml; triiodothyronine, 0.2 nM; glucagon, 2 µg/ml; fibroblast growth factor, 20 ng/ml; and hydrocortisone, testosterone, estradiol, and progesterone at 2 nM each. See Materials and Methods of Chang et al., Proc. Natl. Acad. Sci. USA, Vol. 79, pp. 4795-4799, 1982. See also, page 155 of Barch, M., The ACT Cytogenetics Laboratory Manual, Second edition, 1991.

The present invention provides methods and banks of multipotent stem cells which can be used as tools and/or materials in stem cell research including, the process of differentiation, molecular characterization of the differentiated cells, molecular changes during differentiation, media/factor(s) enhancing the proliferation the multipotent cells, the degree of multipotency of the cells of fibroblast samples, and behaviors of differentiated cells in grafts or transplants. The present invention also provides methods and banks of multipotent stem cells which can be used as tools and/or materials in model systems to study differentiated fibroblast cultures in vitro and their use as immunologically compatible multipotent cells in therapeutics. Such research and study, however, is not needed for practice of the invention.

DEFINITIONS AND OTHER EMBODIMENTS

The term "stem cell" generally refers to an undifferentiated cell that is capable of extensive propagation either in vivo or ex vivo and capable of differentiation to other cell types.

Non-embryonic stem cells, that is, stem cells isolated from a source other than a mammalian embryo, have been isolated, and some of these cells have been found to be multipotent. Non-embryonic cells have been found, for example, in bone marrow, in cord blood (derived from umbilical cords of infants at birth), and in amniotic fluid. Non-embryonic cells are often referred to in various reports as "adult" stem cells, although some suggest that among the postnatal stem cells there may be differences between cells derived from children and from more developmentally mature adults. Two to five milliliters of amniotic fluid, for example, have been reported to contain approximately $1-2 \times 10^4$ live cells per milliliter.

"Fibroblast sample", as described herein comprises fibroblasts and other cell types, including stem cells and other cells and/or their progeny that are capable of multipotency or becoming multipotent. Samples can be obtained by using hollow core needles, for example.

"Multipotent" cells generally can differentiate to form at least one cell type of endodermal, ectodermal, or mesodermal origin. The term "pluripotent cells" generally refers to cells that are able to differentiate into essentially all cell types.

The term "multipotent stem cell", as used herein, refers to a cell that is not itself terminally differentiated (i.e., not at the end of a pathway of differentiation; can divide without limit or at least for the life time of the cell; and when it divides, each daughter cell can either remain as a multipotent stem cell, or embark on a course leading irreversibly to terminal differentiation into cells of any of the three germ layers. The "multipotent stem cell", as used herein, does not refer to embryonic stem cells but rather non-embryonic stem cells, as discussed herein.

The term "collection" refers to several things grouped together or considered as a whole. A collection of cells as described herein refers to a collection of culture, suspension of cells, differentiated cells, multipotent stem cells, pluripotent cells, cells of any of the germ layers, a collection of isolated differentiated or undifferentiated cells, and the like, as understood in the art.

According to an embodiment of the instant invention, a multipotent stem cell from a human skin fibroblast culture has the potential to propagate under suitable conditions during repeated passages in amniotic fluid growth medium (AFM) or any other suitable culture media. The propagated multipotent stem cells from human skin fibroblast culture are capable of differentiation into various cells of a desired germ layer.

The term "passage" with respect to cell culture, as used herein, refers to the aliquoting of a plurality of cells from one culture into a separate container to start a new culture of cells. Typically, passaging comprises the aliquoting of, for example, certain number of cells from one culture in one container into fresh medium in a separate container. The term "passage" also refers to the transfer or subculture of cells from one culture vessel to another. Generally, but not necessarily, this implies subdivisions of a proliferating cell population enabling propagation of a cell line. Thus "passage number" is the number of times a culture has been subcultured. By choosing an appropriate size culture vessel and seeding density, the "passage" of a cell culture can be a matter of convenience for the laboratory, as known in the field, once a week or twice a week, for example. Passage numbers are incremented by one with each subculture in order to keep track of the number of manipulations a particular cell line has undergone. In incrementing passage numbers, the specific number of cells present in the population is generally not considered. In this context, for example, human skin fibroblast culture is repeatedly passaged in amniotic fluid growth medium (AFM) in order to propagate CD117$^+$ cells.

Another approach is the population doubling level (PDL), which is an intrinsic measure of the age of the particular culture of a cell line. In culture, an untransformed cell line has a finite life span expressed in the number of cumulative population doublings that can be achieved. Population doubling levels refer to the total number of times the cells in the population have doubled since their primary isolation in vitro. The formula for calculating PDL is PDL=3.32(log (total viable cells at harvest/total viable cells at seed)). The "life span" of a cell line is plotted as the cumulative PDLs versus time in culture. Subcultures are carried out until the cell line reaches senescence: that is, there is no change in PDL from one subculture to the next.

The term "plasticity", as used herein, referred to a characteristic that reflects the ability of multipotent stem cells to act as progenitor cells that are capable of differentiation into mature cells of any of the three different germ layers. For example, the "plasticity" of multipotent cells in skin fibroblast samples refers to the ability of the cells to propagate and differentiate into a desired type of germ layer cells, such as differentiation into adipose, hepatic, muscle, or nerve tissue.

The term "graft", as used herein, refers to a body part, organ, tissue, or cells. Organs include liver, kidney, pancreas, heart, skin, and lung. Other body parts, such as bone or skeletal matrix, tissue, such as skin, intestines and endocrine glands also are included. Progenitor multipotent stem cells, or progenitor stem cells of various types, are all examples of cells that can be used in grafts. Cells and grafts can be used for tissue and organ regeneration, reconstitution, repopulation, and replacement, and can be autologous to the recipient or type matched to the recipient.

For example, the ability of the hematopoietic stem cells to provide for the lifelong production of all blood lineages is accomplished by a balance between the plasticity of the stem cell, that is the production of committed progenitor cells which generate specific blood lineages, and the replication of the stem cell in the undifferentiated state (self-renewal). The mechanisms regulating the plasticity of the cells and their self-renewal in vivo have been difficult to define. However, the key contributory factors represent a combination of cell intrinsic and environmental influences (Morrison et al., *Proc. Natl. Acad. Sci. USA*, 92: 10302-10306 (1995)).

The terms "about" or "approximately" in the context of numerical values and ranges refers to values or ranges that approximate or are close to the recited values or ranges such that the invention can perform as intended, such as having a desired number or percentage of CD117$^+$ cells, or duration or number of passages allowed in AFM, as is apparent to the skilled person from the teachings contained herein. This is due, at least in part, to the varying culture conditions and the variability of biological systems. Thus, these terms encompass values beyond those resulting from systematic error. These terms make explicit what is implicit.

All ranges set forth herein in the summary and description of the invention include all numbers or values thereabout or therebetween of the numbers of the range. The ranges of the invention expressly denominate and set forth all integers, decimals and fractional values in the range. The term "about" can be used to describe a range.

Each composition and attendant aspects, and each method and attendant aspects, which are described above can be combined with another in a manner consistent with the teachings contained herein. According to the embodiments of the inventions, all methods and the steps in each method can be applied in any order and repeated as many times in a manner consistent with the teachings contained herein.

The invention is further described by the following examples, which do not limit the invention in any manner.

EXAMPLES

Amniotic Fluid Studies on Backup Cultures

Backup amniotic fluid cultures from three patients were received from UMDNJ-New Jersey Medial School. All three patients had fetuses with normal G-banded karyotypes. These samples received in α-MEM with 1% Pen/Strep, 15% FBS, and CHANG MEDIUM® A and B (Irvine Scientific). Upon receipt, the cells were placed in the amniotic fluid growth media (AFM) (as described in De Coppi et al. (2007)) containing: α-MEM (Invitrogen), 15% ES-FBS (Invitrogen), 1% L-glutamine, and 1% Pen/Strep, supplemented with 18% CHANG MEDIUM® B (Irvine Scientific) and 2% CHANG MEDIUM® C (Irvine Scientific). Cultures were maintained at 37° C. with 5% $CO_2$ atmosphere. When the cells reached semi-confluence, they were passaged at least once each week. After a total of 75 days in culture, the percentage of CD117$^+$ cells was examined using phycoerythrin (PE)-labeled monoclonal antibodies to CD117 (Miltenyi Biotec, Auburn, Calif.). Various techniques and media for differentiating stem cells into target cell type are known in the art (see for example, De Coppi et al. (2007); Crigler et al. (*FASEB J.* 21(9):2050-2063 (2007); Chen, et al. *J Cell Sci.* 120:2875-2883, (2007); and Lysy, et al. *Hepatology.* 46(5): 1574-1585, (2007)). These CD117$^+$ cells were then differentiated into adipogenic and nervous tissue following the procedures as described below:

Skin-Derived Fibroblast Studies.

Human fibroblast cultures derived from amniotic fluid and skin of varying age groups were obtained from Coriell Cell Repository (Camden, N.J.). Skin-derived fibroblast cultures were initially grown in Eagle's MEM with Earle's BSS and 15-20% FBS. Upon receipt, the percentage of CD117$^+$ cells in each sample was recorded. All samples were then transferred into AFM. Once CD117+ counts were >85% in each of the samples they were placed in the following culturing conditions for differentiation. The age groups and passage numbers upon receipt and at the start of differentiation are shown in Table 1.

TABLE 1

Passage numbers of fibroblast cells (Coriell Cell Repository) upon arrival and at start of differentiation.

| Origin of fibroblast samples | Arrival | Adipogenic | Hepatic | Muscle | Nerve |
|---|---|---|---|---|---|
| Amniotic fluid | 7 | 11 | 11 | 11 | 11 |
| Prenatal cells | 10 | 15 | 15 | 15 | 14 |
| 3-day-old human (male) | 9 | 13 | 13 | 13 | 13 |
| 11-year-old human (female) | 9 | 13 | 13 | 13 | 12 |
| 37-year-old human (female) | 10 | 14 | 14 | 14 | 14 |
| 96-year-old human (male) | 8 | 12 | 12 | 12 | 12 |

Adipogenic.

Cells were seeded at a density of 3,000 cells/cm$^2$ onto chamber slides (Nunc). They were cultured in DMEM low-glucose medium (Sigma-Aldrich) with 10% FBS (Invitrogen), 1% Pen/Strep, and the following adipogenic supplements: 1 µg/ml dexamethasone (Sigma-Aldrich), 1 mM 3-isobutyl-1-methylxanthine (Sigma-Aldrich), 10 µg/ml insulin (Sigma Aldrich), and 60 µM indomethacin (Sigma-Aldrich). Cells were maintained in adipogenic differentiation media for up to 20 days.

Hepatic.

Cells were seeded at a density of 5,000 cells/cm$^2$ onto chamber slides coated with Matrigel (Sigma-Aldrich). The cells were first expanded for 3 days in AFM then placed in hepatic differentiation media containing: DMEM low-glucose with 15% FBS, 300 µM monothioglycerol (Sigma-Aldrich), 20 ng/ml hepatocyte growth factor (Sigma-Aldrich), 10 ng/ml oncostatin M (Sigma-Aldrich), $10^{-7}$ M dexamethasone (Sigma-Aldrich), 100 ng/ml FGF4 (Peprotech), 1×ITS (Invitrogen) and 1% Pen/Strep. The cells were maintained in this differentiation medium for 17 days, with medium changes every third day.

Myogenic.

Cells were seeded at a density of 3,000 cells/cm$^2$ onto chamber slides coated with Matrigel and grown in DMEM low-glucose with 10% horse serum (Invitrogen), 0.5% chick embryo extract, and 1% Pen/Strep. Twelve hours after seeding, 3 µM 5-aza-2'-deoxycytodine (5-azaC; Sigma-Aldrich) was added to the culture medium for 24 hours. Incubation continued in complete medium lacking 5-azaC, with medium changes every 3 days. Cells were maintained in myogenic differentiation media for up to 20 days.

Neurogenic-Method 1.

Cells were seeded at a concentration of 3,000 cells/cm$^2$ onto chamber slides and cultured in DMEM low-glucose with 2% DMSO, 200 µM BHA (Sigma-Aldrich), 25 ng/ml NGF (Invitrogen), and 1% Pen/Strep. After 2 days, the cells were returned to AFM lacking DMSO and BHA but still containing NGF. Fresh NGF was added every 2 days at a final media concentration of 25 ng/ml for 6 days. The cells were then trypsinized and transferred to chamber slides coated with 1 µg/ml fibronectin and grown overnight in AFM containing 25 ng/ml NGF. After the overnight incubation, the media was changed to DMEM/F12 (Invitrogen) supplemented with N2 (Invitrogen) and 10 ng/ml bFGF (Invitrogen) for 8 days. Fresh bFGF was added every other day.

Neurogenic-Method 2.

Cells were seeded at a concentration of 3,000 cells/cm$^2$ onto either chamber slides or Nunc 6 well Petri dishes for micro array studies. These cells were cultured in DMEM/F12 media (Invitrogen), supplemented with 200 uM BHA (Sigma-Aldrich), N2 (Invitrogene), 25 ng/ml NGF (Invitrogen), 10 ng/ml bFGF (Invitrogen) 15% ES-FBS, 1% Pen/Strep and 1% L-Glutamine. Every two days an additional 25 ng/ml of NGF and 10 ng/ml of bFGF were added to the cultures. After 6 or 7 days the cultures were examined and photographed for nerve morphology or harvested for microarray analysis. The medium used in this Neurogenic-Method 2, referred to as Neurogenic-2, contains no DMSO. A second set of experiments was set up using the above media but without the BHA supplement.

CD117 Immunofluorescent Staining.

The media from the monolayer cultures was removed and cells were washed with HBSS. The cells were then trypsinized and counted using a hemocytometer. An aliquot containing up to $10^7$ cells was taken and used for CD117 staining using a kit supplied by Miltenyi Biotec (Auburn, Calif.). Immunofluorescent staining was done in accordance with the protocol supplied by the manufacturer. Briefly, $10^7$ cells were resuspended in 80 µl of supplied buffer (PBS, 0.5% BSA, and 2 mM EDTA). A 20 µl of FcR blocking reagent was added, followed by 10 µl of CD117 mAb conjugated to phycoerythrin (PE) and incubated for 10 minutes in the dark at 4° C. Cells were then washed with 1 ml of buffer and centrifuged at 300×g for 10 minutes. The cell pellet was resuspended in 1 ml buffer and cell counts were then performed using a Zeiss microscope equipped for phase and fluorescent microscopy (excitation filter 450-490 nm, FT510 dichromatic mirror, barrier filter LP530). Cell counts were done by first locating the cells under phase contrast using a 40× objective, counting the cells in the field and then switching to fluorescent microscopy and recording the numbering in the field that fluoresced. At least 200 cells/sample were recorded at each passage and both low intensity and high intensity fluorescent cells were recorded as positive. The nuclear stem cell marker NANOG was similarly scored with 400 or more cells counted/sample.

Histological Staining.

Cells were fixed in 4% paraformaldehyde in PBS. Adipogenic cells were stained with Oil red O (Sigma-Aldrich) while muscle and hepatic cells were stained with Hematoxylin & Eosin (H&E).

Immunofluorescence.

Cells were fixed in 4% paraformaldehyde in PBS, permeabilized with 0.25% Triton X-100 in PBS (PBST) for 10 minutes, and blocked with 1% BSA in PBST for 30 minutes at 4° C. The cells were then incubated overnight with diluted primary antibodies (1 µg/ml) in 1% BSA in PBST at 4° C., washed, then incubated for 1 hour at room temperature with complementary secondary antibodies (10 µg/ml). Cells were washed then mounted using Vectashield (Vector Laboratories). Anti-human leptin was obtained from Peprotech while nestin, neurofilament-M (NFM), CK18, desmin, and NANOG were obtained from Abcam. The secondary antibodies, both anti-IgG FITC-conjugated, were obtained from Vector Laboratories and Abcam.

Back-Up Amniotic Fluid Cultures.

The percentage of CD117+ cells from the back-up amniotic fluid cultures greatly increased after being passaged for over two months in AFM. At the time of differentiation into adipose and nerve cells, the percentage of CD117+ cells was greater than 50%, with patient A having over 90% CD117+ cells. It was noticed that cells from all three patients were capable of differentiating into either adipose or nervous tissue. While no morphologic differences were observed in the adipose cells that differentiated from the three patient samples (see FIG. 1, *a*), some variations in the mature nerve cell types were noted (see FIG. 1, *b-d*). Patient A and C showed many pyramidal, unipolar, bipolar, and multipolar cells, while patient B produced low percentages of only bipolar and unipolar mature cells, and a large group of cells that were nestin positive but did not have a mature nerve-like morphology (see Table 2).

TABLE 2

Percentages of nerve cell types found in each patient.

| Patient | Pyramidal | Bipolar | Unipolar | Multipolar | Nestin$^+$ Immature Nerve-Like Morphology |
|---|---|---|---|---|---|
| A | 31% | 28% | 21% | 20% | — |
| B | — | 5% | 5% | — | 90% |
| C | 50% | 12% | 13% | 25% | — |

Differentiation of Human Skin-Derived Fibroblasts.

Figure 2:
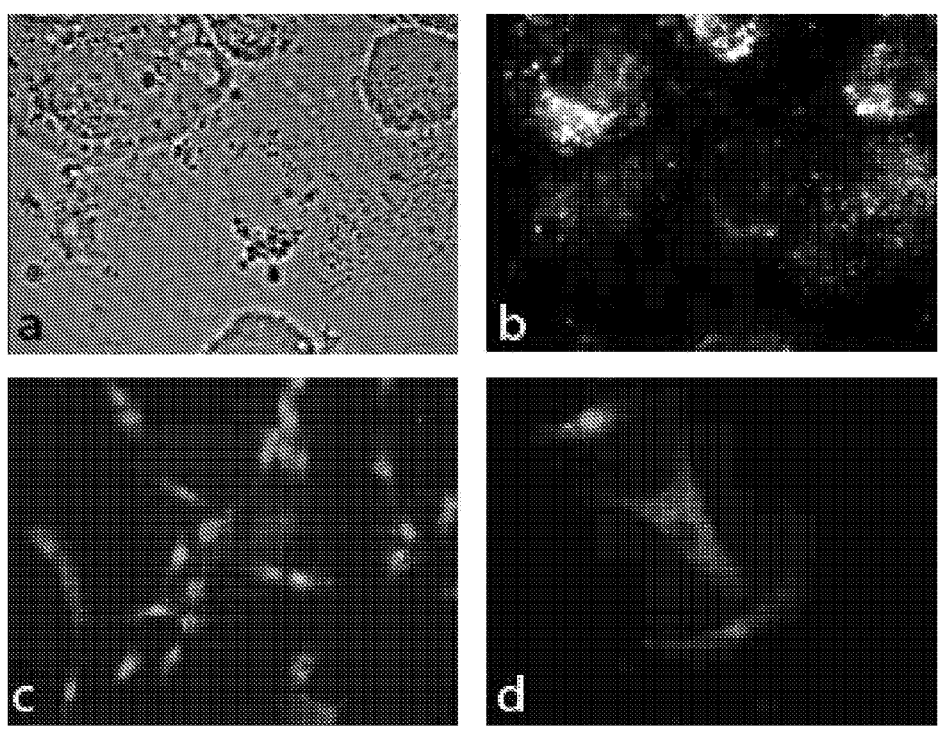
FIG. 2. Characterization of initial fibroblast cultures. a, b: phase contrast and fluorescent representative pictures of CD117$^+$ cells just before differentiation studies, 1000×; showing all the cells CD117$^+$ c, d: representative fluorescent picture for nuclear staining of NANOG also just before differentiation studies, c:200×, d:400×.

One day after the arrival of cell cultures, aliquots from each sample were processed for immunofluorescent microscopy to record the number of CD117$^+$ cells (see FIG. 2 *a, b*). Initial CD117$^+$ cell counts are as follows: amniotic fluid (81%), prenatal cells (79%), 3-day-old (46%), 11-year-old (47%), 37-year-old (23%), and 96-year-old (0.5%). After three passages in AFM, CD117$^+$ cells increased to greater than 85% in all samples. The initial fibroblasts were also stained with the nuclear stem cell marker NANOG (see FIG. 2 *c, d*) and greater than 85% of the cells from each sample were also positive for this marker. At this point, differentiation into adipose, hepatic, muscle, and nerve tissue was examined.

Figure 3:
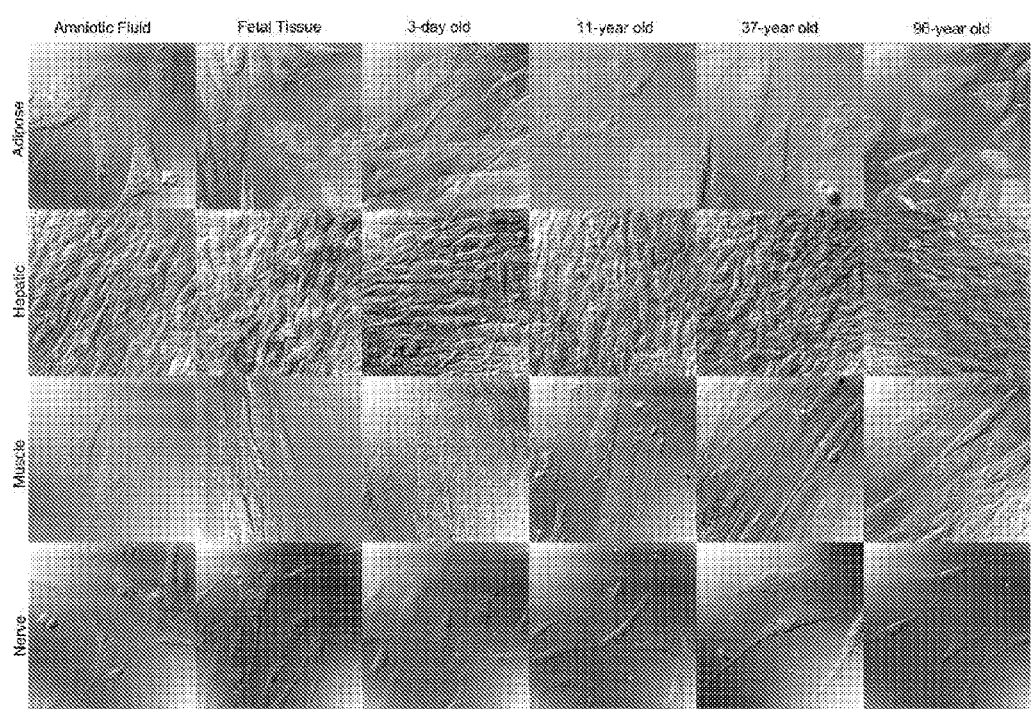
FIG. 3. Differentiated cells from amniotic fluid and skin fibroblasts obtained from individuals belonging to varying age groups. Representative DIC pictures taken at 400×.

FIG. 3 illustrates the endpoint of differentiation of these patients' cells showing differential interference contrast (DIC) pictures from each patient and the appearance of the differentiated adipose, hepatic, muscle, and nerve cells. A good deal of uniformity of the differentiated cells for each tissue type from each age sample was observed. Appearance of granular vesicles in all of the adipose samples was noted. The hepatic cells were polygonal shaped and also contained numerous granular vesicles within each cell. The differentiated muscle cells contained filamentous-like structures and the appearance of multi-nucleated cells was also noted.

Figure 4:
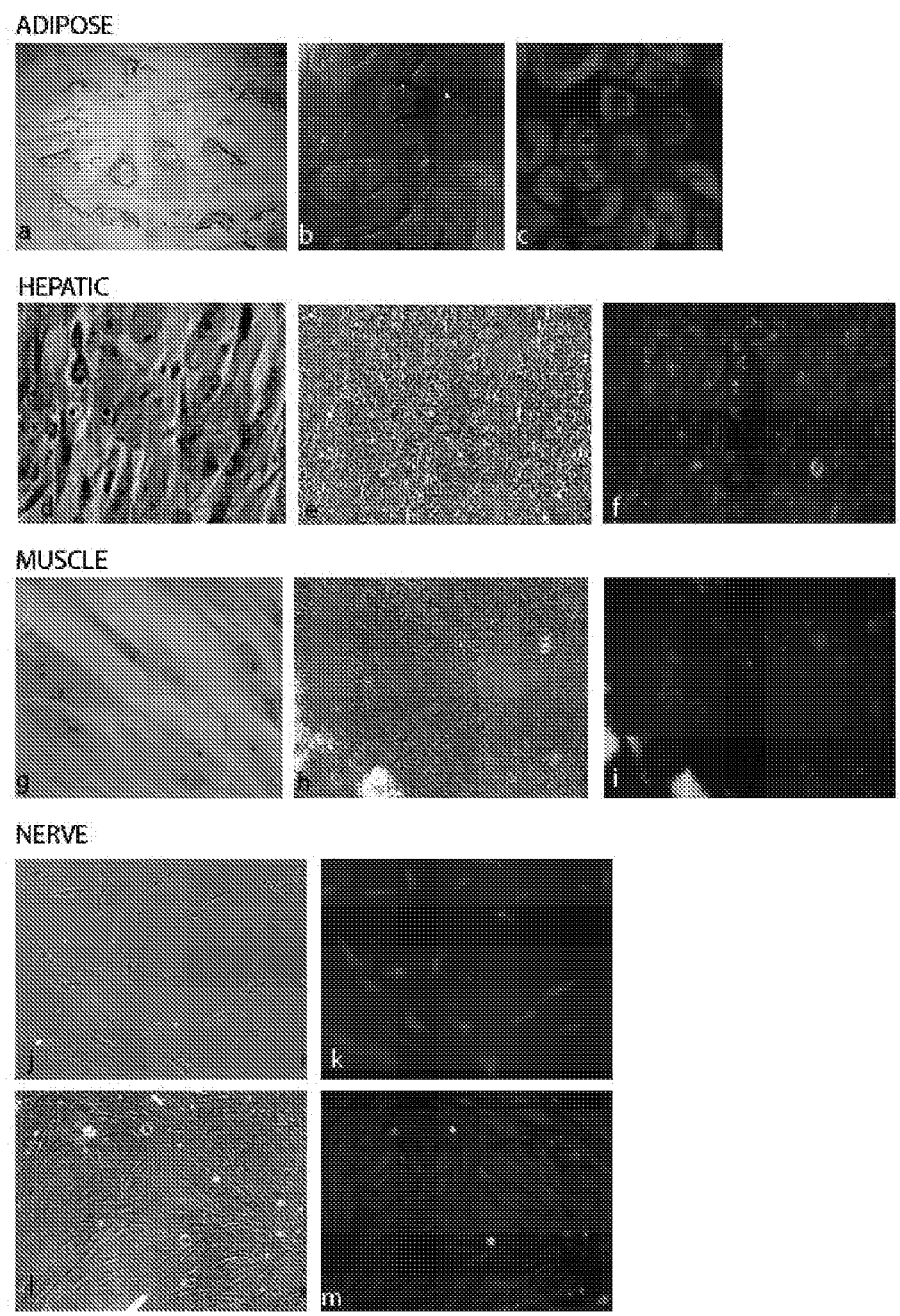
FIG. 4. Differentiated cells from skin fibroblast sample of a 96-year-old human. a: representative picture of adipose cells stained with Oil red O, 200×; b, c: DIC and fluorescent picture of adipose cells stained with FITC-conjugated leptin, 400×; d: representative picture of Hematoxylin & Eosin (H&E) stained hepatic tissue, 480×; e, f: phase contrast and fluorescent picture of hepatic cells stained with FITC-conjugated CK18, 200×; g: representative picture of H&E stained muscle tissue 480×; h, i: phase contrast and fluorescent picture of muscle cells stained with FITC-conjugated desmin, 200×; j, k: phase contrast and fluorescent picture of nerve cells stained with FITC-conjugated NFM, 200×; l, m: phase contrast and fluorescent picture of nerve cells stained with FITC-conjugated nestin, 200×.

FIG. 4 shows the results using various staining methods performed on the cells from the 96-year-old Caucasian male. The staining patterns seen in this age sample were essentially the same as those seen in the other age groups. The nerve cells were positive for nestin and NFM. Adipose cells showed lipid accumulation using Oil Red O and granular structures were positive for leptin. The hepatic cells had a typical morphology using Hematoxylin & Eosin (H&E) staining, were positive for hepatic marker CK18. Muscle cells also had typical H&E staining appearance and were positive for a muscle marker desmin.

Figure 5:
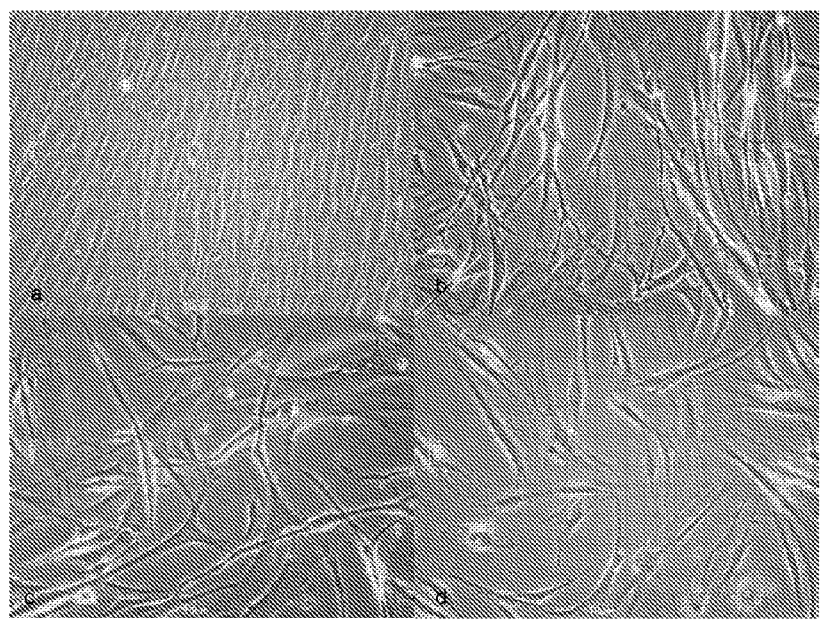
FIG. 5 depicts undifferentiated cells grown in AFM (5a) or differentiated cells grown in Neurogenic-Medium 2 DMEM/F-12 supplemented with BHA, N2, ES-FCS-Pen/Strep, L-Glutamine, NGF and bFGF (5b and 5c) or Neurogenic-Medium 2 without BHA (5d). All photomicroscope pictures were taken at 10×, phase contrast.

FIG. 5 shows the results using Neurogenic—Method 2 on differentiating fibroblasts into cells having a nerve like cell morphology. In this method, no DMSO was used, since DMSO has been implicated in creating cells that have a nerve like morphology, because of a collapsing of internal cytoskeleton components. In this figure fibroblasts from the same patient sample were seeded into a six well Petri dish at the same cell density, and looked at after 6 days in culture. In one well the cells were grown in AFM, in an adjacent well they were grown in the media formulated in the Neurogenetic-Method 2 that contained DMEM/F-12 media supplemented with BHA, N2, ES-FCS-Pen/Strep, L-Glutamine, NGF and bFGF. In another adjacent well, the cells were grown in this Neurogenic-2 medium without BHA. As can be seen in FIG. 5, cells grown in AMF reached full confluence after six days and looked like one would expect from an undifferentiated fibroblast culture not having any growth factors added (FIG. 5*a*). Cells grown in Neurogenic-2 medium, with all the above supplements showed a different morphology after six days in culture that had a nerve-like appearance (FIGS. 5*b* and 5*c*). These cultures showed cells having very long cytoplasmic extensions, some reaching many hundreds of micrometers in length, which are morphologic structures one sees in the axon and dendrite extensions of nerves. Cells grown in the Neurogenic-Method 2 medium without BHA, showed a very different morphology at 6 days, with cells that resembled astrocytes, that is, another nerve like cell type but not neurons.

Astrocytes (also known collectively as astroglia) are characteristic star-shaped glial cell in the brain and spinal cord. They perform many functions, including biochemical support of endothelial cells which form the blood-brain barrier, the provision of nutrients to the nervous tissue, and a principal role in the repair and scarring process of the brain and spinal cord following traumatic injuries. Astrocytes are now widely regarded as cells that propagate intercellular $Ca^{2+}$ waves over long distances in response to stimulation, and, similar to neurons, release transmitters (called gliotransmitters) in a $Ca^{2+}$-dependent manner.

Microarray Studies and Gene Expression Profiling:

Gene expression profiling was performed using the Affymetrix GENECHIP® (Affymetrix GENECHIP® microarray technology) Human Gene 1.0 ST Array. This array interrogates 28,869 well-annotated transcripts with 764,885 distinct probes. RNA was isolated from three independent experiments using the Qiagen RNeasy mini kit. RNA was converted to cDNA following the Affymetrix Expression Analysis Whole Transcript (WT) Sense Target Labeling Protocol. Briefly, total RNA (300 ng) underwent a 1st and 2nd strand cDNA synthesis. cRNA was obtained by an in vitro transcription reaction which was then used as the template for generating a 1st strand cDNA. The cDNA was fragmented and end-labeled with biotin. The biotin labeled cDNA was hybridized to the Human Gene 1.0 ST Array for 16 hours at 45° C. using the GENECHIP® Hybridization Oven 640. Washing and staining with Streptavidin-phycoerythrin was performed using the GENECHIP® Fluidics Station 450. Images were acquired using the Affymetrix Scanner 3000 7G Plus.

The array data was analyzed using Partek Genomic Suite software (Partek Inc., St. Louis, Mo.). This software supports the most commonly used methods for microarray data normalization and analysis. The software offers highly optimized statistical methods and interactive 2-D and 3-D graphics, and provides a broad range of parametric and nonparametric statistical methods as well as data mining algorithms for classification and prediction. Importantly annotation of all results is possible with links to public genomic resources such as the UCSC Genome Browser, GenBank®, NCBI GEO, and NetAffx™.

The data was first normalized using quantile normalization with the RMA algorithm (25,261) for gene-level intensities. Principal Component Analysis was performed to check consistency of the experiments to determine if there was any obvious chip outlier. Support trees, hierarchical clustering and K-means support clustering of the transcripts was performed to group samples and genes with similar expression patterns. Paired t-tests to find significant genes up or down regulated at each time point when compared to their initial starting profile. The data was correct for multiple testing and false discovery rate using the Benjamini-Hochberg's method when appropriate. Functional annotations, pathways and interactions were examined using Ingenuity Pathway Analysis (IPA). Utilizing the Ingenuity Pathways Knowledge Base, were able to examine functional annotations, curated pathways and interactions, as well identify associations from the literature and build pathway models to examine the sequence of events leading to differentiation.

Microarray Results:

The results of the microarray experiments are shown in a tabular format for Adipose (Table 3), Muscle (Table 3), Hepatic (Table 4) and Neurogenic (Table 4) cells. Basically, each of these Tables shows a spread sheet with genes that were either up or down regulated in the tissues analyzed using Microarrays for some 27,000 genes. Tabular data show only the group of genes that were different from the undifferentiated control cells (see Tables 3 and 4). Genes that responded with at least two fold up or down regulation (a 2× difference) were identified. These results show for the three tissues:

1) Different genes are found to be up or down regulated in the different morphologic types. These gene sets are distinct from each other and different from the undifferentiated cells.
2) The cells from each age group act the same when differentiated, regardless of the source of the sample, whether from an embryo or from an old man, they reacted the same way and appeared to turn on or off the same genes when they went down the differentiation pathway. Cells were grown under the conditions described herein. The conditions and the process used to grow the cells can be used as a useful model system for the study of these different gene pathways for drug development and/or future studies of differentiation.
3) Information on each gene, as recorded in the Tables 3 and 4, of what each gene has been implicated in doing, can be obtained by referring to the indicated public domain databases at the end of the tables.
4) In biology, structure and function are linked. It is observed that the changes in gene expression lead to morphologic changes. There may be and probably are other gene pathways that are important in getting functionality of the tissue types.
5) The DiCopi medium (Neurogenic #1) for nerve differentiation, which contained DMSO, while showing nerve like cells on microscopic observations, on microarray analysis did not show much gene expression differences in a comparison of undifferentiated vs. differentiated cells. However, use of Neurogenic #2 medium, without DMSO and without fibronectin coated slides, did show differentiation into cells having a nerve morphology (see FIGS. 5b and 5c), as well as showing a considerable number of up and down regulated genes, with expression levels that were two or more fold different in the differentiated vs. the undifferentiated cells (see Table 4).

Multipotent Stem Cell Bank:

The present invention provides cultures using human skin fibroblast samples that when expanded by propagating multipotent stem cells in an appropriate culture medium, such as an amniotic fluid medium (AFM) for several passages yield large number of CD117+ cells. These cells can further be differentiated into cells of any of the three germ layers, for examples, cells can be differentiated cells into adipocytes, heptocytes, muscle, and nervous cell types. The differentiated cells can be used for regeneration of desired tissues and organs. For example, cells can be used for autologous therapies based on propagated multipotent stem cells for regeneration of tissues, for use as grafts, tissue/organ replacement or supplementation. In order to facilitate the availability of multipotent stem cells for regeneration into desired tissues or organs, multipotent stem cell banks can be established from multipotent stem cells derived from human skin fibroblast samples. Human skin fibroblast sample-derived multipotent stem cells for the cell bank can be obtained by various method of collecting fibroblast samples from human skin tissue biopsy.

Skin tissue biopsy samples can be obtained from any layers of human skin, such as endoderm, ectoderm, or mesoderm. For example, skin samples can be collected from lower layers of human skin through a hollow core to the skin layer to obtain samples containing amounts of skin fibroblasts and other cells (for example, fibroblast samples obtained from a 3 mm punch biopsy of the mesial aspect of the upper left arm, see US Publication No. 20040071749).

Following the collection of the tissue biopsy sample, the initial step in the isolation, proliferation and/or selective expansion of the tissue-specific progenitor multipotent stem cells present in a tissue biopsy involves the culturing of the tissue biopsy. The tissue biopsy can be subjected to physical and/or chemical dissociating means capable of dissociating cellular stratum in the tissue sample. Methods for dissociating cellular layers within the tissues are well known in the field. For example, the dissociating means may be either a physical and/or a chemical disruption means. Physical dissociation means might include, for example, scraping the tissue biopsy with a scalpel, mincing the tissue, physically cutting the layers apart, or perfusing the tissue with enzymes. Chemical dissociation means might include, for example, digestion with enzymes such as trypsin, dispase, collagenase, trypsin-EDTA, thermolysin, pronase, hyaluronidase, elastase, papain and pancreatin. Non-enzymatic solutions for the dissociation of tissue also can be used.

The dissociation of the tissue biopsy can be achieved by placing the tissue biopsy in a pre-warmed enzyme solution containing an amount of trypsin sufficient to dissociate the cellular stratum in the tissue biopsy. The enzyme solution used in the method is preferably calcium and magnesium free. Tissue biopsy derived from human skin (comprising epithelial and dermal cells) are generally treated with solution containing trypsin in an amount preferably between about 5 and 0.1% trypsin per volume of the solution for between 5 to 60 minutes. More preferably, the trypsin concentration of the solution is about 2.5 to 0.25% for 15 to 20 minutes.

Following immersion of the tissues in the trypsin solution for an appropriate amount of time, the dissociated cells are removed and suspended in a suitable culture medium. There are a large number of culture media that exist for culturing tissue from animals. Examples of media include, Eagle's Minimal Essential Medium (MEM), Dulbecco's Modified Eagle's Medium (DMEM), RPMI 1640, F-12, IMDM, Alpha Medium and McCoy's Medium. For example, samples are treated with collagenase to process the sample for a primary culture. Collagenase treated samples containing fibroblast samples are further purified by centrifuge at 300 g for 15 min, and the yielded pellets are washed at least twice with Eagle's minimal essential medium (MEM) to remove blood and cell debris.

Cells are grown in Eagle's MEM supplemented with 10% fetal bovine serum (FBS), 100 U/ml penicillin and 100 mg/ml streptomycin in a 37° C., 5% $CO_2$/95% air environment. After reaching confluence, cells are sub-cultivated with 0.25% trypsin in MEM with no added $Ca^{2+}$ or $Mg^{2+}$.

Isolated fibroblast cultures are grown in human amniotic fluid medium (AFM) containing α-MEM (Invitrogen), 15% ES-FBS (Invitrogen), 1% L-glutamine, and 1% Pen/Strep, supplemented with 18% CHANG MEDIUM® B (Irvine Scientific) and 2% CHANG MEDIUM® C (Irvine Scientific). Cultures are maintained at 37° C. with 5% $CO_2$ atmosphere. When the cells reached semi-confluence, they are passaged at least once each week. After a total of 75 days in culture, the percentage of $CD117^+$ cells is examined using PE-labeled monoclonal antibodies to CD117 (Miltenyi Biotec, Auburn, Calif.). A morphologically homogeneous population of human multipotent stem cells can be obtained at this stage. These multipotent stem cells are maintained in a humidified atmosphere in an incubator under 5% $CO_2$ at 37° C., which are subsequently preserved in a bank of human multipotent stem cells and can be stored under suitable conditions, such as cryopreservation.

These $CD117^+$ human multipotent stem cells from the bank can be further differentiated into cells of any of the desired cell types following media and techniques disclosed herein, or by any of the methods known in the art, for differentiating stem cells into target cell types. Autologous and type matched grafting, regeneration, and repopulation on a wide scale is thus made possible by the present invention.

Many reports indicate that mammalian skin of the mature animal contains small numbers of cells that have the capacity to differentiate into various mature cell types. These multipotent cells are likely to be harbored in the hair follicles and/or the dermis of the skin. Other reports indicate that amniotic fluid is a source of multipotent stem cells, while others, show that the introduction of specific genes into fibroblasts using retroviruses can reprogram such cells into pluripotent stem cells. The present invention provides use different selection procedures to isolate stem cells and provide ways to manipulate them in various ways to permit differentiation without reprogramming the cells. For instance, De Coppi et al. (2007) used microbeads coated with anti-CD117 to isolate $CD117^+$ cells from back-up amniotic fluid cultures and used such cells for differentiation studies.

According to one embodiment of this invention, instead of immediately using microbeads to select for $CD117^+$ cells from the backup amniocentesis samples, the cells were cultured for an extended period of time, preferably more than two months. At the end of this time period, according to the invention the $CD117^+$ cell count greatly increased in each patient sample. According to the invention, it was found that amniotic fluid cells that have been passaged were capable of differentiation into nerve and adipose tissue when placed in the appropriate differentiation media.

The disclosed in various embodiments show that human fibroblast cultures, if permitted to stay in culture for several passages in adequately supplemented growth media, contain large numbers of cells having surface and nuclear markers linked to stem cells, CD117 and NANOG, respectively. These cells can further be differentiated into adipocytes, hepatocytes, muscle, and nervous cells that morphologically resemble such differentiated cell types.

According to the instant invention, initial selection using immunologic microbeads or flow cytometry methods are not necessary, and the cells are not exposed to any retroviruses.

The instant process also does not involve reprogramming of these cells using exogenous genes or viruses (for example, retrovirus, retroviral construct with human genes, or the like), instead, the process generally involves two steps. The first of which enhances the number of $CD117^+$ cells in the cultures, and the second of which selects cells that can be differentiated into various cell types under the appropriate culture conditions.

The multipoint cells observed, according to one embodiment, do not need any special feeder layer for growth. The cells grow as a monolayer and are easily transferred into the standard media used for differentiation studies. The multipotent cells are easily obtained from frozen fibroblast cultures originating from various ages. While some cellular variation was observed between the different age samples, the differentiated cells show four distinct and different cell types, corresponding to the morphological appearance and staining characteristics of adipose, hepatic, muscle, and nervous tissue.

The presence of $CD117^+$ cells in fibroblast samples at the noted passage numbers as studied had not been observed before. Miettinen and Lasota (see *Appl Immunohistochem Mol Morphol.* 13 (3): 205-220, 2005) reported that fibroblast samples are a good negative control for CD117 staining procedures. It was also reported that variability and poor reproducibility of staining has been a prevalent problem, especially with polyclonal antisera, and that this has led to significant data heterogeneity. According the instant invention, it was made certain that CD117 staining and counting protocol are consistent, as the same PE-labeled monoclonal CD117 antibody, the same dilutions, and the same fluorescent microscope were used. It was observed that a wide range of positive CD117 cells in all the initial cultures, with much higher $CD117^+$ in the amniotic fluid and prenatal cells cultures than that seen in the older age samples. It was also observed that after being in the AFM for multiple (more than one, preferably at least three) passages, all the age samples had over 85% CD117 positive cells. The findings supported to conclude that in addition to the factors stated by Mietten and Lasota (2005), other factors also can influence the number of $CD117^+$ cells observed in fibroblast cultures, such as the age of the specimen, the culture passage number, culture conditions that the cells are grown in, and possibly even the cell makeup of the ampoule that was originally frozen from the patient.

It is noted that the fluorescent microscope used in this study has a wide range for excitation (450-490 nm) and permits emissions of 530 nm or grater to be observed as epi-fluorescence. While these parameters permit a reading of PE conjugated CD117+ cells (typical peek excitation at 488 nm and emission at 575 nm), also can be non specific to excite non PE stained molecules that might auto fluoresce because of cellular activation caused by the action of CD117, or because of other factors like confluence, which can produce auto fluorescence in fibroblast cultures.

The finding that at the $7^{th}$ passage, 81% CD117+ cells were present in the amniotic fluid samples received from the repository, further confirmed the instant findings that numerous $CD117^+$ cells can be found in amniotic fluid cultures at this passage number.

Also, the observation that it only took a few passages in AFM after arrival from the repository, for all the aged samples to obtain over 85% CD117 positive cells, was of special interest. Because of this quick transition, it appeared that the first step in seeing a large increase of $CD117^+$ cells could be one where the gene for the CD117 surface marker is activated. It is believed that there is a factor or factors in the AFM that acts to upregulate the CD117 gene leading to increased surface expression of the CD117 marker, which enhances their proliferation and differentiation potential.

Fibroblast cells are known to produce stem cell factor (SCF), which is the ligand for CD117. CD117 is a transmembranic type III receptor tyrosine kinase. When SCF binds with the CD117 receptor, a phosphorylation cascade is activated which in turn regulates cellular activities in different cells, including apoptosis, cell differentiation, proliferation, chemotaxis, and cell adhesion (Miettinen, M., Lasota, J. (2005)). Therefore, it is possible that the advanced culture passage, or use of the AFM, or some combination of the two, produces a genetic activation of the CD117 gene, which can produce the CD117 protein receptor. Since fibroblasts produce SCF, the conditions are then set up in the culture for the cells to start a phosphorylation cascade that leads to the ability to differentiate into the different cell types when placed in a suitable medium.

The ability of adult stem cells to act as progenitor cells capable of "transdifferentiation" into mature cells of the three different germ layers has been under active investigation, with studies of the hematopoietic stem cell (HSC) being noteworthy. Several reports have claimed that HSCs can, under appropriate reconstruction conditions in vivo, be transformed into not only blood cells but also muscle cells (both skeletal myocytes and cardiomyocytes), brain cells, liver cells, skin cells, lung cells, kidney cells, intestinal cells, and pancreatic cells (see *Regenerative Medicine*. Department of Health and Human Services. August 2006.). While the above studies are not without controversy, they do support the idea that there is a wide "plasticity" to the range of cells that might be possible with adult stem cells and that the conditions and/or environmental niches that adult stem cells occupy are critical to the differentiation that is observed. However, the "plasticity" of multipotent cells from fibroblasts were not addressed or appreciated until the instant investigation.

The present investigation raises the interesting possibility that the multipotent cells from cultured fibroblast samples may also have a large degree of "plasticity." The cells that exist at the passage numbers used in the instant experiments (and from a wide range of age donors), can differentiate into several cellular directions when placed in the appropriate culture environment. This illustrates the importance of the environmental conditions cells are grown in and the potential differentiated cells can have for altered fates.

The results obtained from this investigation are basically morphological, which are based on microscopic observations of the cellular changes seen in tissue culture and the staining characteristics of the differentiated cells. There are obviously four distinct and different cell types that are seen after the various culturing procedures. However, these cultured cells may not have a molecular profile that is exactly the same as that seen in vivo for adipose, hepatic, muscle, and nerve cells.

The process described herein can be used as a simple in vitro model system to study various gene pathways that are modified during cellular differentiation in general. Such a process can provide a way to test the effects of different agents in both normal and abnormal cells on many gene pathways. An experiment using fibroblasts from a patient and the patient's carrier mother, with the X-linked gene for Duchene's Muscular Dystrophy, indicates that fibroblasts from these individuals can show a muscle like appearance using the differentiation procedures.

Embodiments of the present invention provide examples for methods of making multipotent stem cells from human skin fibroblast samples and tissue biopsies obtained from humans. However, the invention is not limited to human applications. Biopsy tissue samples can be obtained from any animal, including humans. Preferably, the animal is a mammal from the one of the mammalian orders. The mammalian orders include Monotremata, Metatheria, Didelphimorphia, Paucituberculata, Microbiotheria, Dasyuromorphia, Peraamelemorphia, Notoryctemorphia, Diprotodontia, Insectivora, Macroscelidea, Scandentia, Dermoptera, Chiroptera, Primates, Xenarthra, Pholidota, Lagomorpha, Rodentia, Cetacea, Carnivora, Tubulidentata, Proboscidea, Hyracoidea, Sirenia, Perissodactyla and Artiodactyla. Non-human mammals include dogs, cats, cattle, horse, sheep, and non-human primates.

In one embodiment, the tissue biopsies may be obtained from different tissues or organs, e.g., skin, lung, pancreas, liver, stomach, intestine, heart, reproductive organs, bladder, kidney, urethra and other urinary organs, etc.

In another embodiment, the multipotent stem cells propagated from different animals and/or organs have the capacity to be further differentiate terminally to various cell types, including osteoblast, chondrocyte, adipocyte, fibroblast, marrow stroma, skeletal muscle, smooth muscle, cardiac muscle, occular, endothelial, epithelial, hepatic, pancreatic, hematopoietic, glial, neuronal or oligodendrocyte cell type.

TABLE 3

Gene expression profiles of differentiated v. undifferentiated cell types.*

| Adipose vs. Undifferentiated cells | | | | Muscle vs. Undifferentiated cells | | | |
| --- | --- | --- | --- | --- | --- | --- | --- |
| Probe Set ID | Gene Symbol | mRNA Accession | Fold change in expression | Probe Set ID | Gene Symbol | mRNA Accession | Fold change in expression |
| 8125919 | FKBP5 | NM_004117 | 15.4 | 7914342 | FABP3 | NM_004102 | 12.9 |
| 8066822 | SULF2 | NM_018837 | 10.5 | 8092970 | APOD | NM_001647 | 7.97 |
| 7962559 | SLC38A4 | NM_018018 | 6.1 | 8133876 | CD36 | NM_001001547 | 7.58 |
| 7929438 | HELLS | NM_018063 | −3.5 | 8068353 | SLC5A3 | NM_006933 | 5.26 |
| 8151816 | GEM | NM_005261 | −4.4 | 8111941 | HMGCS1 | NM_001098272 | 5.32 |
| 8062766 | MYBL2 | NM_002466 | −2.7 | 8068361 | SLC5A3 | NM_006933 | 6.07 |
| 7956658 | SLC16A7 | NM_004731 | −3.9 | 8095728 | EREG | NM_001432 | 6.2 |
| 8023575 | CCBE1 | NM_133459 | −5.5 | 8103254 | SFRP2 | NM_003013 | 5.07 |
| 7985829 | FANCI | NM_018193 | −4.7 | 8013341 | MFAP4 | NM_002404 | 5.15 |
| 8154491 | ADAMTSL1 | NM_052866 | −4.8 | 8148070 | COL14A1 | NM_021110 | 7.34 |
| 8118669 | KIFC1 | NM_002263 | −3.9 | 7966026 | NUAK1 | NM_014840 | 4.73 |
| 8046461 | ZAK | NM_133646 | −3.4 | 8092691 | BCL6 | NM_001706 | 4.01 |
| 8097356 | PLK4 | NM_014264 | −4.5 | 8000636 | LOC728888 | XR_015889 | 4.66 |
| 7953291 | CD9 | NM_001769 | −6.5 | 7950067 | DHCR7 | NM_001360 | 4.07 |
| 8043602 | NCAPH | NM_015341 | −5.0 | 7951351 | PDGFD | NM_025208 | 4.69 |
| 7992789 | TNFRSF12A | NM_016639 | −2.9 | 8178435 | IER3 | NM_003897 | 4.71 |
| 7910022 | CNIH3 | NM_152495 | −5.5 | 7904726 | TXNIP | NM_006472 | 3.92 |
| 7973067 | NP | NM_000270 | −3.7 | 8179704 | IER3 | NM_003897 | 4.42 |
| 8145570 | ESCO2 | NM_001017420 | −5.3 | 8124848 | IER3 | NM_003897 | 4.42 |

TABLE 3-continued

Gene expression profiles of differentiated v. undifferentiated cell types.*

| | Adipose vs. Undifferentiated cells | | | | Muscle vs. Undifferentiated cells | | |
|---|---|---|---|---|---|---|---|
| Probe Set ID | Gene Symbol | mRNA Accession | Fold change in expression | Probe Set ID | Gene Symbol | mRNA Accession | Fold change in expression |
| 7933469 | ARHGAP22 | NM_021226 | −3.6 | 8057677 | SLC40A1 | NM_014585 | 7.99 |
| 8114572 | HBEGF | NM_001945 | −6.6 | 8176234 | CLIC2 | NM_001289 | 3.62 |
| 8129458 | ARHGAP18 | NM_033515 | −3.5 | 8126853 | C6orf138 | NM_001013732 | 4.14 |
| 8144153 | NCAPG2 | NM_017760 | −4.5 | 8022640 | DHFR | NM_000791 | −2.86 |
| 8157691 | — | ENST00000373683 | −3.6 | 8054479 | MALL | NM_005434 | −6.49 |
| 8132557 | AEBP1 | NM_001129 | −3.6 | 7951284 | MMP3 | NM_002422 | −5.39 |
| 7981514 | AHNAK2 | BC090889 | −3.8 | 7912692 | HSPB7 | NM_014424 | −3.19 |
| 7906085 | LMNA | NM_170707 | −3.2 | 8118086 | TCF19 | NM_007109 | −3.4 |
| 7909967 | CAPN2 | NM_001748 | −3.7 | 8177747 | TCF19 | NM_007109 | −3.4 |
| 8046380 | ITGA6 | NM_000210 | −8.1 | 8151871 | CCNE2 | NM_057749 | −4.03 |
| 8100298 | OCIAD2 | NM_001014446 | −4.8 | 8124391 | HIST1H2AB | NM_003513 | −3.67 |
| 8008237 | ITGA3 | NM_002204 | −5.0 | 7983306 | WDR76 | NM_024908 | −3.89 |
| 7966878 | CIT | NM_007174 | −6.3 | 8043602 | NCAPH | NM_015341 | −4.24 |
| 7928429 | PLAU | NM_002658 | −3.2 | 7919642 | HIST2H2AB | NM_175065 | −3.46 |
| 7901010 | KIF2C | NM_006845 | −5.9 | 8145418 | CDCA2 | NM_152562 | −2.96 |
| 8085754 | SGOL1 | NM_001012410 | −4.8 | 8179228 | TCF19 | NM_001077511 | −3.48 |
| 8180307 | — | NM_145903.1 | −5.5 | 8060813 | MCM8 | NM_032485 | −3.25 |
| 7924096 | NEK2 | NM_002497 | −5.4 | 8168794 | CENPI | NM_006733 | −3.76 |
| 8047467 | ALS2CR7 | NM_139158 | −3.8 | 7960340 | FOXM1 | NM_202002 | −4.07 |
| 8065637 | COMMD7 | NM_001099339 | −3.1 | 8144153 | NCAPG2 | NM_017760 | −3.35 |
| 8147756 | BAALC | NM_024812 | −4.5 | 8063043 | UBE2C | NM_181802 | −3.16 |
| 8135990 | FLNC | NM_001458 | −4.2 | 8124531 | HIST1H3I | NM_003533 | −3.71 |
| 8030007 | EMP3 | NM_001425 | −4.3 | 8034122 | SPC24 | NM_182513 | −3.63 |
| 7982663 | BUB1B | NM_001211 | −6.5 | 8103932 | MLF1IP | NM_024629 | −4.31 |
| 8124527 | HIST1H1B | NM_005322 | −5.4 | 7965535 | DUSP6 | NM_001946 | −5.9 |
| 8063043 | UBE2C | NM_181802 | −3.5 | 7923426 | UBE2T | NM_014176 | −3.74 |
| 8085138 | — | ENST00000355170 | −7.7 | 7986068 | BLM | NM_000057 | −3.34 |
| 8131631 | HDAC9 | NM_178423 | −3.4 | 7937020 | MKI67 | NM_002417 | −5.19 |
| 8126428 | TRERF1 | ENST00000372922 | −4.1 | 7933707 | ZWINT | NM_032997 | −3.58 |
| 7970569 | SACS | NM_014363 | −3.2 | 8091411 | TM4SF1 | NM_014220 | −5.64 |
| 8083941 | ECT2 | NM_018098 | −4.3 | 8077731 | FANCD2 | NM_033084 | −3.36 |
| 8017651 | SMURF2 | NM_022739 | −5.3 | 8072687 | MCM5 | NM_006739 | −4.4 |
| 7917182 | ELTD1 | NM_022159 | −4.2 | 8168146 | KIF4A | NM_012310 | −4.88 |
| 8017133 | FAM33A | BC017873 | −3.3 | 7968563 | RFC3 | NM_002915 | −2.96 |
| 8040578 | CENPO | NM_024322 | −3.2 | 8047288 | SGOL2 | NM_152524 | −3.7 |
| 7982757 | CASC5 | NM_170589 | −7.8 | 8017262 | BRIP1 | NM_032043 | −3.29 |
| 8125059 | CLIC1 | NM_001288 | −3.8 | 8124534 | HIST1H4L | NM_003546 | −3.4 |
| 8179564 | KIFC1 | NM_002263 | −4.6 | 7984540 | KIF23 | NM_138555 | −3.59 |
| 8013671 | SPAG5 | NM_006461 | −4.6 | 8018849 | TK1 | NM_003258 | −4.85 |
| 8090433 | MGLL | NM_007283 | −5.4 | 7982792 | RAD51 | NM_002875 | −3.46 |
| 8108301 | KIF20A | NM_005733 | −10.7 | 8043036 | — | ENST00000307796 | −3.09 |
| 8154692 | TEK | NM_000459 | −6.8 | 8059834 | DKFZp762E1312 | NM_018410 | −4.09 |
| 7983157 | TMEM62 | NM_024956 | −3.5 | 7914851 | CLSPN | NM_022111 | −4.42 |
| 7963280 | LOC57228 | NM_001033873 | −6.0 | 8079237 | KIF15 | NM_020242 | −4.3 |
| 8037374 | PLAUR | NM_002659 | −4.1 | 8109712 | HMMR | NM_012484 | −5.44 |
| 8091411 | TM4SF1 | NM_014220 | −5.6 | 8117368 | HIST1H4C | NM_003542 | −3.96 |
| 8007071 | CDC6 | NM_001254 | −5.7 | 8071212 | CDC45L | NM_003504 | −3.7 |
| 8096808 | CCDC109B | NM_017918 | −3.9 | 8067167 | AURKA | NM_198433 | −3.93 |
| 8089372 | KIAA1524 | NM_020890 | −4.3 | 8109639 | PTTG1 | NM_004219 | −4.23 |
| 7960340 | FOXM1 | NM_202002 | −6.3 | 7923189 | KIF14 | NM_014875 | −3.76 |
| 8112376 | CENPK | NM_022145 | −4.7 | 8145570 | ESCO2 | NM_001017420 | −5.05 |
| 8178598 | CLIC1 | NM_001288 | −4.0 | 8093500 | TACC3 | NM_006342 | −4.12 |
| 8019857 | NDC80 | NM_006101 | −6.4 | 7929258 | KIF11 | NM_004523 | −4.5 |
| 8107100 | RGMB | NM_001012761 | −5.8 | 8091757 | TRIM59 | NM_173084 | −3.54 |
| 8179827 | CLIC1 | NM_001288 | −4.0 | 8173506 | ERCC6L | NM_017669 | −4.85 |
| 8168794 | CENPI | NM_006733 | −6.3 | 8061564 | ID1 | NM_181353 | −6.15 |
| 8026300 | CD97 | NM_078481 | −4.1 | 7991406 | PRC1 | NM_003981 | −4.93 |
| 8180308 | — | NM_145905.1 | −6.0 | 7927710 | CDC2 | NM_001786 | −5.88 |
| 7914878 | — | AY605064 | −7.3 | 8102076 | CENPE | NM_001813 | −3.93 |
| 8134552 | ARPC1B | NM_005720 | −3.4 | 7982358 | ARHGAP11A | NM_014783 | −3.71 |
| 7923189 | KIF14 | NM_014875 | −5.4 | 8130374 | FBXO5 | NM_012177 | −4.5 |
| 7948332 | LPXN | NM_004811 | −12.3 | 7982889 | NUSAP1 | NM_016359 | −5.28 |
| 7947248 | KIF18A | NM_031217 | −4.7 | 7971866 | DIAPH3 | NM_001042517 | −4.36 |
| 7954090 | EMP1 | NM_001423 | −6.6 | 8085754 | SGOL1 | NM_001012410 | −5.08 |
| 7944082 | TAGLN | NM_001001522 | −3.9 | 8014974 | TOP2A | NM_001067 | −5.39 |
| 8054702 | CKAP2L | NM_152515 | −5.9 | 8061471 | GINS1 | BC012542 | −4.22 |
| 8144880 | SH2D4A | NM_022071 | −5.4 | 8124380 | HIST1H1A | NM_005325 | −4.29 |
| 7929258 | KIF11 | NM_004523 | −5.5 | 8021187 | C18orf24 | NM_001039535 | −5.72 |
| 7957850 | GAS2L3 | NM_174942 | −4.2 | 8124527 | HIST1H1B | NM_005322 | −4.85 |
| 8091757 | TRIM59 | NM_173084 | −3.8 | 8107706 | LMNB1 | NM_005573 | −4.19 |
| 8053417 | CAPG | NM_001747 | −4.1 | 7947248 | KIF18A | NM_031217 | −4.65 |
| 7953218 | RAD51AP1 | NM_006479 | −6.0 | 7974404 | CDKN3 | NM_005192 | −7.3 |

TABLE 3-continued

Gene expression profiles of differentiated v. undifferentiated cell types.*

| Adipose vs. Undifferentiated cells | | | | Muscle vs. Undifferentiated cells | | | |
|---|---|---|---|---|---|---|---|
| Probe Set ID | Gene Symbol | mRNA Accession | Fold change in expression | Probe Set ID | Gene Symbol | mRNA Accession | Fold change in expression |
| 7909568 | DTL | NM_016448 | −7.6 | 8061579 | TPX2 | NM_012112 | −4.41 |
| 7983306 | WDR76 | NM_024908 | −5.1 | 7909568 | DTL | NM_016448 | −5.33 |
| 8017262 | BRIP1 | NM_032043 | −5.2 | 7910997 | EXO1 | NM_130398 | −4.93 |
| 8095585 | SLC4A4 | NM_001098484 | −4.6 | 8155214 | MELK | NM_014791 | −4.41 |
| 7982889 | NUSAP1 | NM_016359 | −4.8 | 8056572 | SPC25 | NM_020675 | −8.52 |
| 8163063 | CTNNAL1 | NM_003798 | −4.8 | 7929334 | CEP55 | NM_018131 | −6.43 |
| 8029006 | AXL | NM_021913 | −4.1 | 7929078 | MPHOSPH1 | NM_016195 | −3.71 |
| 7994109 | PLK1 | NM_005030 | −6.8 | 7924096 | NEK2 | NM_002497 | −5.09 |
| 8105267 | ITGA2 | NM_002203 | −5.7 | 8013671 | SPAG5 | NM_006461 | −5.05 |
| 8005171 | TRPV2 | NM_016113 | −5.8 | 7982757 | CASC5 | NM_170589 | −7.2 |
| 7958253 | — | ENST00000310995 | −5.8 | 8112376 | CENPK | NM_022145 | −4.54 |
| 8008784 | PRR11 | NM_018304 | −6.5 | 8008784 | PRR11 | NM_018304 | −4.82 |
| 8114536 | TMEM173 | ENST00000330794 | −4.0 | 8132318 | ANLN | NM_018685 | −7.59 |
| 7990545 | CSPG4 | NM_001897 | −7.6 | 8054702 | CKAP2L | NM_152515 | −5.68 |
| 8168146 | KIF4A | NM_012310 | −7.1 | 8040223 | RRM2 | NM_001034 | −6.46 |
| 8154245 | PDCD1LG2 | NM_025239 | −8.5 | 7953218 | RAD51AP1 | NM_006479 | −5.95 |
| 7909708 | CENPF | NM_016343 | −6.3 | 8097356 | PLK4 | NM_014264 | −5.14 |
| 8059413 | DOCK10 | NM_014689 | −5.6 | 8105828 | CCNB1 | NM_031966 | −6.12 |
| 7916898 | DEPDC1 | NM_017779 | −7.3 | 7900699 | CDC20 | NM_001255 | −6.97 |
| 8061579 | TPX2 | NM_012112 | −9.0 | 8104234 | TRIP13 | NM_004237 | −5.29 |
| 8072687 | MCM5 | NM_006739 | −5.4 | 8102560 | MAD2L1 | NM_002358 | −4.88 |
| 7983969 | CCNB2 | NM_004701 | −9.8 | 8089372 | KIAA1524 | NM_020890 | −4.14 |
| 7929334 | CEP55 | NM_018131 | −9.2 | 7970513 | C13orf3 | NM_145061 | −7.27 |
| 8155849 | ANXA1 | NM_000700 | −4.3 | 7989647 | KIAA0101 | NM_014736 | −7.54 |
| 8014974 | TOP2A | NM_001067 | −6.3 | 8019857 | NDC80 | NM_006101 | −6.8 |
| 8056572 | SPC25 | NM_020675 | −7.4 | 8124388 | HIST1H3B | NM_003537 | −7.75 |
| 7954527 | ARNTL2 | NM_020183 | −8.1 | 7914878 | — | AY605064 | −8.08 |
| 7916112 | RAB3B | NM_002867 | −8.5 | 8108301 | KIF20A | NM_005733 | −8 |
| 8054580 | BUB1 | NM_004336 | −9.0 | 8054580 | BUB1 | NM_004336 | −7.39 |
| 8104234 | TRIP13 | NM_004237 | −5.9 | 7982663 | BUB1B | NM_001211 | −6.5 |
| 7921099 | CRABP2 | NM_001878 | −5.7 | 8094278 | NCAPG | NM_022346 | −7.7 |
| 7991406 | PRC1 | NM_003981 | −9.5 | 8120838 | TTK | NM_003318 | −7.05 |
| 8120838 | TTK | NM_003318 | −6.1 | 8152617 | HAS2 | NM_005328 | −6.92 |
| 8049544 | — | ENST00000308482 | −4.2 | 8102643 | CCNA2 | NM_001237 | −6.6 |
| 7923086 | ASPM | NM_018136 | −11.7 | 8117594 | HIST1H2BM | NM_003521 | −12.1 |
| 8123006 | SYNJ2 | NM_003898 | −4.5 | 7994109 | PLK1 | NM_005030 | −7.55 |
| 8130505 | VIL2 | NM_003379 | −4.4 | 7923086 | ASPM | NM_018136 | −7.68 |
| 8149955 | PBK | NM_018492 | −13.6 | 7901010 | KIF2C | NM_006845 | −6.84 |
| 8120967 | NT5E | NM_002526 | −7.4 | 8149955 | PBK | NM_018492 | −8.76 |
| 7951284 | MMP3 | NM_002422 | −10.8 | 7916898 | DEPDC1 | NM_017779 | −9.55 |
| 8135601 | MET | NM_000245 | −6.3 | 7979307 | DLG7 | NM_014750 | −11.3 |
| 7920291 | S100A16 | NM_080388 | −4.5 | 7983969 | CCNB2 | NM_004701 | −8.1 |
| 7927710 | CDC2 | NM_001786 | −7.2 | 8001133 | SHCBP1 | NM_024745 | −8.19 |
| 7937020 | MKI67 | NM_002417 | −11.6 | 7906930 | NUF2 | NM_145697 | −12.3 |
| 7934570 | KCNMA1 | NM_001014797 | −4.6 | | | | |
| 8124388 | HIST1H3B | NM_003537 | −8.8 | | | | |
| 7971866 | DIAPH3 | NM_001042517 | −7.9 | | | | |
| 8154512 | ADAMTSL1 | NM_001040272 | −5.6 | | | | |
| 8067167 | AURKA | NM_198433 | −5.1 | | | | |
| 7984540 | KIF23 | NM_138555 | −7.6 | | | | |
| 8155214 | MELK | NM_014791 | −8.0 | | | | |
| 8117594 | HIST1H2BM | NM_003521 | −13.7 | | | | |
| 8021635 | SERPINB2 | NM_002575 | −28.7 | | | | |
| 8091678 | VEPH1 | NM_024621 | −6.4 | | | | |
| 7957260 | GLIPR1 | NM_006851 | −8.3 | | | | |
| 7906930 | NUF2 | NM_145697 | −16.3 | | | | |
| 8086517 | CDCP1 | NM_022842 | −9.7 | | | | |
| 8135734 | FLJ21986 | ENST00000310396 | −10.6 | | | | |
| 8094278 | NCAPG | NM_022346 | −11.3 | | | | |
| 8001133 | SHCBP1 | NM_024745 | −13.2 | | | | |
| 7989647 | KIAA0101 | NM_014736 | −13.0 | | | | |
| 8132318 | ANLN | NM_018685 | −15.9 | | | | |
| 8023497 | ATP8B1 | NM_005603 | −9.4 | | | | |
| 7979307 | DLG7 | NM_014750 | −17.2 | | | | |
| 8040223 | RRM2 | NM_001034 | −9.4 | | | | |
| 8021623 | SERPINB7 | NM_003784 | −10.0 | | | | |
| 7951271 | MMP1 | NM_002421 | −30.0 | | | | |
| 7976567 | BDKRB1 | NM_000710 | −22.2 | | | | |

*Additional information and data related to the genes listed in the Table are available in public domain and can be obtained from various publicly available databases including, GenBank, UniGene and RefSeq. Data obtained by using Affymetrix GENECHIP ® microarray technology.

TABLE 4

Gene expression profiles of differentiated v. undifferentiated cell types.*

| Hepatic vs. Undifferentiated cells | | | | Neurogenic vs. Undifferentiated cells | | | |
|---|---|---|---|---|---|---|---|
| Probe Set ID | Gene Symbol | mRNA Accession | Fold change in expression | Probe Set ID | Gene Symbol | mRNA Accession | Fold change in expression |
| 8180303 | — | NM_030754.2 | 27.81 | 7915612 | — | — | 26.22 |
| 8092970 | APOD | NM_001647 | 19.96 | 8135943 | — | — | 22.01 |
| 8100154 | CORIN | NM_006587 | 18.25 | 7897801 | RNU5E | NR_002754 | 20.14 |
| 8125919 | FKBP5 | NM_004117 | 17.76 | 8000636 | LOC728888 | XR_015889 | 19.17 |
| 8142270 | NRCAM | NM_001037132 | 15.6 | 8169634 | — | — | 11.36 |
| 7906417 | CADM3 | NM_021189 | 13.75 | 7946567 | — | ENST00000386723 | 6.68 |
| 8095744 | AREG | NM_001657 | 13.67 | 8053797 | — | ENST00000357042 | 6.58 |
| 8171359 | GPM6B | NM_001001995 | 12.78 | 7919598 | LOC729135 | XM_001133556 | 6.31 |
| 8174361 | TSC22D3 | NM_198057 | 12.38 | 8108422 | — | — | 5.92 |
| 7955441 | METTL7A | NM_014033 | 9.124 | 8079163 | — | — | 5.50 |
| 8135915 | HIG2 | NM_013332 | 8.949 | 7894611 | — | — | 5.14 |
| 8162388 | OMD | NM_005014 | 8.823 | 7939432 | — | — | 4.91 |
| 8161884 | PRUNE2 | NM_138818 | 8.381 | 8152333 | — | — | 4.76 |
| 7962058 | TMTC1 | NM_175861 | 8.223 | 8081878 | — | — | 4.68 |
| 8111569 | RANBP3L | NM_145000 | 8.008 | 8161476 | — | BC011779 | 4.59 |
| 7943413 | BIRC3 | NM_001165 | 7.876 | 7959925 | — | — | 4.08 |
| 7907286 | FMO1 | NM_002021 | 7.829 | 7967705 | — | — | 4.08 |
| 8111915 | SEPP1 | NM_005410 | 7.635 | 8154225 | — | ENST00000387463 | 4.00 |
| 8095736 | AREG | ENST00000264487 | 7.611 | 8121782 | — | — | 3.90 |
| 7943984 | ZBTB16 | NM_006006 | 7.587 | 7995320 | — | — | 3.87 |
| 8122265 | TNFAIP3 | NM_006290 | 7.47 | 7901967 | — | — | 3.74 |
| 7898693 | ALPL | NM_000478 | 7.387 | 7958200 | EID3 | NM_001008394 | 3.71 |
| 8152703 | FBXO32 | NM_058229 | 7.334 | 8180259 | — | NM_198555.3 | 3.67 |
| 8092691 | BCL6 | NM_001706 | 6.055 | 8049237 | — | — | 3.56 |
| 7951077 | SESN3 | NM_144665 | 6.045 | 8168161 | — | — | 3.56 |
| 7964834 | CPM | NM_001005502 | 6.042 | 7969048 | — | AK097860 | 3.45 |
| 7971486 | — | ENST00000389909 | 5.902 | 8081620 | TAGLN3 | NM_013259 | 3.44 |
| 8161865 | PRUNE2 | BC022571 | 5.891 | 7896388 | — | — | 3.28 |
| 7929816 | SCD | NM_005063 | 5.695 | 7995328 | — | — | 3.18 |
| 7934916 | CH25H | NM_003956 | 5.692 | 8043687 | ANKRD36 | BC128517 | 3.14 |
| 8025601 | ICAM1 | NM_000201 | 5.585 | 7946849 | — | — | 2.96 |
| 7978644 | NFKBIA | NM_020529 | 5.499 | 8141166 | — | ENST00000333502 | 2.90 |
| 8089011 | — | ENST00000340162 | 5.497 | 8121273 | — | ENST00000365516 | 2.90 |
| 7968789 | C13orf15 | NM_014059 | 5.34 | 8176091 | — | uc004fle.1 | 2.82 |
| 8095680 | IL8 | NM_000584 | 5.33 | 7899071 | — | — | 2.79 |
| 8000636 | LOC728888 | XR_015889 | 5.223 | 7934997 | PPP1R3C | NM_005398 | −2.46 |
| 7948612 | FADS1 | NM_013402 | 5.223 | 7944049 | SIDT2 | NM_001040455 | −2.49 |
| 8114010 | IRF1 | NM_002198 | 4.994 | 7910111 | EPHX1 | NM_000120 | −2.59 |
| 8089015 | PROS1 | NM_000313 | 4.933 | 7909801 | LYPLAL1 | NM_138794 | −2.60 |
| 8117020 | MYLIP | NM_013262 | 4.878 | 7955694 | IGFBP6 | NM_002178 | −2.60 |
| 8081386 | NFKBIZ | NM_031419 | 4.853 | 7901969 | ROR1 | NM_005012 | −2.61 |
| 7933204 | C10orf126 | NM_007021 | 4.833 | 7918426 | SLC16A1 | NM_004696 | −2.74 |
| 8111941 | HMGCS1 | NM_001098272 | 4.833 | 8138776 | HIBADH | NM_152740 | −2.75 |
| 8101699 | — | AK092450 | 4.805 | 8092691 | BCL6 | NM_001706 | −2.84 |
| 7918064 | COL11A1 | NM_080629 | 4.798 | 7939120 | RCN1 | NM_002901 | −2.86 |
| 8021470 | PMAIP1 | NM_021127 | 4.679 | 7928354 | KIAA0974 | BC015394 | −2.91 |
| 8121949 | LAMA2 | NM_000426 | 4.642 | 7997904 | — | ENST00000378337 | −2.92 |
| 8130578 | SNORA20 | NR_002960 | 4.586 | 8047401 | — | AK124664 | −2.92 |
| 7928308 | DDIT4 | NM_019058 | 4.565 | 8051993 | PIGF | NM_173074 | −2.92 |
| 7987163 | — | ENST00000320930 | 4.508 | 8018975 | LGALS3BP | NM_005567 | −2.98 |
| 7940028 | SERPING1 | NM_000062 | 4.404 | 8082075 | DTX3L | NM_138287 | −3.01 |
| 8069252 | PCBP3 | NM_020528 | 4.271 | 8000998 | VKORC1 | NM_024006 | −3.01 |
| 8057578 | CALCRL | NM_005795 | 4.27 | 7940565 | FADS2 | NM_004265 | −3.04 |
| 8128123 | RRAGD | NM_021244 | 4.16 | 8163637 | TNC | NM_002160 | −3.04 |
| 8106516 | JMY | NM_152405 | 4.084 | 7951662 | CRYAB | NM_001885 | −3.05 |
| 7950067 | DHCR7 | NM_001360 | 4.077 | 7968928 | — | ENST00000379050 | −3.06 |
| 7902541 | IFI44L | NM_006820 | 4.045 | 7938687 | NUCB2 | NM_005013 | −3.08 |
| 8077490 | LMCD1 | NM_014583 | 3.951 | 7952408 | SIAE | NM_170601 | −3.09 |
| 8154951 | — | GENSCAN00000020724 | 3.87 | 7983811 | PIGB | NM_004855 | −3.09 |
| 7966026 | NUAK1 | NM_014840 | 3.837 | 8041508 | QPCT | NM_012413 | −3.10 |
| 8045688 | TNFAIP6 | NM_007115 | 3.73 | 8150565 | RNF170 | NM_030954 | −3.10 |
| 8127201 | COL21A1 | NM_030820 | 3.638 | 7909586 | PPP2R5A | NM_006243 | −3.11 |
| 7902527 | PTGFR | NM_001039585 | 3.608 | 8917728 | RPL5 | U66589 | −3.12 |
| 7920642 | MUC1 | NM_001018016 | 3.548 | 8062174 | ERGIC3 | NM_198398 | −3.16 |
| 8077376 | ITPR1 | NM_002222 | 3.538 | 7961365 | MANSC1 | NM_018050 | −3.16 |
| 8025828 | LDLR | NM_000527 | 3.5 | 7901951 | PGM1 | NM_002633 | −3.20 |
| 7898057 | PDPN | NM_006474 | 3.488 | 7927681 | BICC1 | NM_001080512 | −3.21 |
| 8048864 | CCL20 | NM_004591 | 3.471 | 8113073 | ARRDC3 | NM_020801 | −3.21 |
| 8148280 | SQLE | NM_003129 | 3.368 | 7910494 | ARV1 | NM_022786 | −3.22 |
| 8162276 | NFIL3 | NM_005384 | 3.257 | 8107673 | GRAMD3 | NM_023927 | −3.25 |
| 7986293 | MCTP2 | NM_018349 | 3.192 | 8123463 | — | ENST00000332290 | −3.26 |
| 8162283 | ROR2 | NM_004560 | 3.124 | 8097098 | USP53 | NM_019050 | −3.27 |

TABLE 4-continued

Gene expression profiles of differentiated v. undifferentiated cell types.*

| Hepatic vs. Undifferentiated cells | | | | Neurogenic vs. Undifferentiated cells | | | |
|---|---|---|---|---|---|---|---|
| Probe Set ID | Gene Symbol | mRNA Accession | Fold change in expression | Probe Set ID | Gene Symbol | mRNA Accession | Fold change in expression |
| 7922689 | GLUL | NM_002065 | 3.012 | 8098328 | GALNT7 | NM_017423 | -3.29 |
| 7922130 | DPT | NM_001937 | 2.971 | 7917240 | CTBS | NM_004388 | -3.32 |
| 7914202 | — | ENST00000373828 | 2.911 | 8169580 | IL13RA1 | NM_001560 | -3.34 |
| 8117321 | TRIM38 | NM_006355 | 2.899 | 8111255 | CDH10 | NM_006727 | -3.37 |
| 8166278 | SCML1 | NM_001037540 | 2.863 | 8160637 | B4GALT1 | NM_001497 | -3.38 |
| 8043310 | RMND5A | NM_022780 | 2.843 | 8026047 | JUNB | NM_002229 | -3.41 |
| 8140686 | SEMA3D | NM_152754 | -2.56 | 7979085 | PYGL | NM_002863 | -3.45 |
| 8010061 | SPHK1 | NM_182965 | -2.67 | 8083978 | NAALADL2 | NM_207015 | -3.48 |
| 8154512 | ADAMTSL1 | NM_001040272 | -2.92 | 8115099 | PDGFRB | NM_002609 | -3.48 |
| 7900510 | CTPS | NM_001905 | -2.97 | 7918474 | — | ENST00000286692 | -3.49 |
| 8112902 | DHFR | NM_000791 | -3.03 | 7908777 | — | GENSCAN00000061939 | -3.50 |
| 7941214 | POLA2 | NM_002689 | -3.06 | 8045587 | ACVR2A | NM_001616 | -3.53 |
| 7990545 | CSPG4 | NM_001897 | -3.11 | 8089015 | PROS1 | NM_000313 | -3.54 |
| 8020495 | CABLES1 | NM_138375 | -3.13 | 8155169 | RECK | NM_021111 | -3.56 |
| 8029006 | AXL | NM_021913 | -3.14 | 7950731 | PRCP | NM_199418 | -3.57 |
| 8022640 | DHFR | NM_000791 | -3.19 | 8101648 | HSD17B11 | NM_016245 | -3.63 |
| 8123006 | SYNJ2 | NM_003898 | -3.23 | 8122396 | AIG1 | NM_016108 | -3.63 |
| 8050240 | ODC1 | NM_002539 | -3.24 | 7980958 | LGMN | NM_005606 | -3.64 |
| 8021623 | SERPINB7 | NM_003784 | -3.33 | 8131871 | CCDC126 | NM_138771 | -3.64 |
| 8124391 | HIST1H2AB | NM_003513 | -3.42 | 8175531 | CDR1 | NM_004065 | -3.64 |
| 8034122 | SPC24 | NM_182513 | -3.44 | 8121588 | DSE | NM_001080976 | -3.64 |
| 7968563 | RFC3 | NM_002915 | -3.47 | 8157021 | NIPSNAP3A | NM_015469 | -3.65 |
| 8145418 | CDCA2 | NM_152562 | -3.52 | 8131539 | TMEM106B | ENST00000336176 | -3.66 |
| 7982792 | RAD51 | NM_002875 | -3.61 | 8089759 | TMEM39A | NM_018266 | -3.68 |
| 7984330 | ZWILCH | NR_003105 | -3.61 | 7935251 | TCTN3 | NM_001013840 | -3.69 |
| 7908543 | NEK7 | NM_133494 | -3.63 | 7974229 | KLHDC2 | NM_014315 | -3.71 |
| 8159642 | TUBB2C | NM_006088 | -3.64 | 8001211 | ITFG1 | NM_030790 | -3.72 |
| 8063043 | UBE2C | NM_181802 | -3.67 | 8086538 | LOC644714 | BC047037 | -3.74 |
| 7929438 | HELLS | NM_018063 | -3.72 | 7903294 | HIAT1 | NM_033055 | -3.75 |
| 8061471 | GINS1 | BC012542 | -3.72 | 8161423 | — | ENST00000377549 | -3.77 |
| 8059838 | DKFZp762E1312 | NM_018410 | -3.72 | 8161455 | — | ENST00000377517 | -3.77 |
| 7963157 | RACGAP1 | NM_013277 | -3.73 | 8155487 | KGFLP1 | XM_001127435 | -3.77 |
| 8135601 | MET | NM_000245 | -3.75 | 8041781 | EPAS1 | NM_001430 | -3.81 |
| 8105267 | ITGA2 | NM_002203 | -3.78 | 8098195 | SC4MOL | NM_006745 | -3.82 |
| 8071212 | CDC45L | NM_003504 | -3.8 | 7927658 | UBE2D1 | NM_003338 | -3.82 |
| 7955179 | TUBA1C | NM_032704 | -3.8 | 8059376 | SERPINE2 | NM_006216 | -3.82 |
| 7944722 | STS-1 | NM_032873 | -3.83 | 7932964 | C1D | NM_173177 | -3.83 |
| 8124531 | HIST1H3I | NM_003533 | -3.84 | 8129573 | MOXD1 | NM_015529 | -3.85 |
| 8173732 | TAF9B | NM_015975 | -3.86 | 7908459 | CFH | NM_000186 | -3.88 |
| 8176263 | TAF9B | NM_015975 | -3.86 | 8095110 | KIT | NM_001093772 | -3.88 |
| 8124534 | HIST1H4L | NM_003546 | -3.88 | 7956613 | TSPAN31 | NM_005981 | -3.95 |
| 7933707 | ZWINT | NM_032997 | -3.94 | 8113250 | ARTS-1 | NM_001040458 | -3.99 |
| 8095585 | SLC4A4 | NM_001098484 | -3.94 | 8127425 | LMBRD1 | NM_018368 | -4.03 |
| 7919642 | HIST2H2AB | NM_175065 | -3.94 | 8157038 | SLC44A1 | NM_080546 | -4.04 |
| 8168794 | CENPI | NM_006733 | -3.96 | 7916493 | PPAP2B | NM_003713 | -4.05 |
| 8017262 | BRIP1 | NM_032043 | -3.98 | 8105040 | OSMR | NM_003999 | -4.08 |
| 7921033 | IQGAP3 | NM_178229 | -4.01 | 8129861 | IFNGR1 | NM_000416 | -4.12 |
| 8107706 | LMNB1 | NM_005573 | -4.01 | 8045835 | GALNT5 | NM_014568 | -4.23 |
| 8089372 | KIAA1524 | NM_020890 | -4.03 | 8067839 | — | ENST00000332473 | -4.24 |
| 7913869 | STMN1 | NM_203401 | -4.05 | 8056102 | CD302 | NM_014880 | -4.24 |
| 7965335 | DUSP6 | NM_001946 | -4.06 | 8115691 | SLIT3 | NM_003062 | -4.25 |
| 8098423 | NEIL3 | NM_018248 | -4.07 | 8103389 | CTSO | NM_001334 | -4.26 |
| 8102076 | CENPE | NM_001813 | -4.1 | 8104758 | — | ENST00000326958 | -4.28 |
| 8130374 | FBXO5 | NM_012177 | -4.15 | 8112107 | PPAP2A | NM_003711 | -4.29 |
| 7971104 | TRPC4 | NM_016179 | -4.16 | 7934920 | LIPA | NM_000235 | -4.30 |
| 8118669 | KIFC1 | NM_002263 | -4.17 | 7969613 | GPC6 | NM_005708 | -4.35 |
| 7923426 | UBE2T | NM_014176 | -4.24 | 7983630 | FGF7 | NM_002009 | -4.35 |
| 7919591 | — | ENST00000369175 | -4.26 | 7960730 | MBOAT5 | NM_005768 | -4.41 |
| 8155214 | MELK | NM_014791 | -4.3 | 7929816 | SCD | NM_005063 | -4.41 |
| 8100347 | SCFD2 | NM_152540 | -4.3 | 8108370 | EGR1 | NM_001964 | -4.42 |
| 7934570 | KCNMA1 | NM_001014797 | -4.36 | 7909730 | KCNK2 | NM_001017425 | -4.47 |
| 8093500 | TACC3 | NM_006342 | -4.37 | 8094228 | BST1 | NM_004334 | -4.51 |
| 8013671 | SPAG5 | NM_006461 | -4.39 | 8127563 | COL12A1 | NM_004370 | -4.52 |
| 8117368 | HIST1H4C | NM_003542 | -4.4 | 8037231 | PSG3 | ENST00000327495 | -4.57 |
| 8102560 | MAD2L1 | NM_002358 | -4.49 | 8149551 | PSD3 | NM_206909 | -4.63 |
| 7923189 | KIF14 | NM_014875 | -4.56 | 8091283 | PLOD2 | NM_182943 | -4.88 |
| 8152668 | ATAD2 | NM_014109 | -4.56 | 8112668 | GCNT4 | NM_016591 | -5.01 |
| 8120654 | KCNQ5 | NM_019842 | -4.64 | 8180318 | — | NM_173211.1 | -5.09 |
| 8103932 | MLF1IP | NM_024629 | -4.67 | 8180317 | — | NM_173210.1 | -5.16 |
| 8152512 | TNFRSF11B | NM_002546 | -4.7 | 8043995 | IL1R1 | NM_000877 | -5.19 |
| 7913655 | ID3 | NM_002167 | -4.71 | 7922051 | CREG1 | NM_003851 | -5.21 |
| 8173506 | ERCC6L | NM_017669 | -4.71 | 7943998 | NNMT | NM_006169 | -5.32 |

TABLE 4-continued

Gene expression profiles of differentiated v. undifferentiated cell types.*

| | Hepatic vs. Undifferentiated cells | | | | Neurogenic vs. Undifferentiated cells | | |
|---|---|---|---|---|---|---|---|
| Probe Set ID | Gene Symbol | mRNA Accession | Fold change in expression | Probe Set ID | Gene Symbol | mRNA Accession | Fold change in expression |
| 7914851 | CLSPN | NM_022111 | −4.74 | 7958019 | DRAM | NM_018370 | −5.42 |
| 8037272 | PSG5 | NM_002781 | −4.77 | 8089011 | — | ENST00000340162 | −5.52 |
| 7955694 | IGFBP6 | NM_002178 | −4.79 | 7986383 | IGF1R | NM_000875 | −5.57 |
| 8124380 | HIST1H1A | NM_005325 | −4.81 | 8130867 | THBS2 | NM_003247 | −5.70 |
| 7983306 | WDR76 | NM_024908 | −4.82 | 8037272 | PSG5 | NM_002781 | −5.70 |
| 7909708 | CENPF | NM_016343 | −4.89 | 8056257 | FAP | NM_004460 | −5.71 |
| 8037231 | PSG3 | ENST00000327495 | −4.94 | 7930454 | PDCD4 | NM_145341 | −5.71 |
| 8179564 | KIFC1 | NM_002263 | −4.94 | 7909142 | — | ENST00000362067 | −5.80 |
| 8018849 | TK1 | NM_003258 | −4.96 | 8013341 | MFAP4 | NM_002404 | −6.31 |
| 7971866 | DIAPH3 | NM_001042517 | −4.99 | 8046922 | COL3A1 | NM_000090 | −6.45 |
| 8072687 | MCM5 | NM_006739 | −5.01 | 7934278 | P4HA1 | NM_000917 | −6.58 |
| 7940147 | FAM111B | ENST00000343597 | −5.04 | 7965410 | DCN | NM_133503 | −6.86 |
| 8151871 | CCNE2 | NM_057749 | −5.06 | 8090509 | — | ENST00000309047 | −6.95 |
| 8021187 | C18orf24 | NM_001039535 | −5.1 | 8081288 | TMEM45A | NM_018004 | −7.02 |
| 7966878 | CIT | NM_007174 | −5.1 | 7942957 | PRSS23 | NM_007173 | −7.03 |
| 8075635 | — | X77690 | −5.15 | 7963575 | — | ENST00000328474 | −7.62 |
| 8085754 | SGOL1 | NM_001012410 | −5.2 | 7953603 | C1S | NM_201442 | −7.63 |
| 7912692 | HSPB7 | NM_014424 | −5.27 | 8152522 | ENPP2 | NM_006209 | −7.70 |
| 8083887 | CLDN11 | NM_005602 | −5.27 | 8146863 | SULF1 | NM_015170 | −7.76 |
| 8154692 | TEK | NM_000459 | −5.28 | 8163672 | DIPAS | AY623011 | −7.81 |
| 7984765 | KIF23 | NM_138555 | −5.29 | 8121749 | GJA1 | NM_000165 | −7.85 |
| 8043602 | NCAPH | NM_015341 | −5.32 | 8109752 | ODZ2 | NM_001080428 | −8.05 |
| 7910997 | EXO1 | NM_130398 | −5.38 | 8089145 | ABI3BP | NM_015429 | −8.35 |
| 8112376 | CENPK | NM_022145 | −5.48 | 7960919 | MFAP5 | NM_003480 | −8.71 |
| 7916112 | RAB3B | NM_002867 | −5.51 | 7960744 | C1R | NM_001733 | −9.07 |
| 8109639 | PTTG1 | NM_004219 | −5.55 | 8075635 | — | X77690 | −9.51 |
| 7982889 | NUSAP1 | NM_016359 | −5.55 | 7985317 | KIAA1199 | NM_018689 | −11.08 |
| 8019842 | TYMS | NM_001071 | −5.56 | 8051583 | CYP1B1 | NM_000104 | −13.01 |
| 8097356 | PLK4 | NM_014264 | −5.68 | 8112980 | EDIL3 | NM_005711 | −13.27 |
| 8067167 | AURKA | NM_198433 | −5.71 | 7965403 | LUM | NM_002345 | −17.15 |
| 8073062 | APOBEC3B | NM_004900 | −5.82 | 8052355 | EFEMP1 | NM_004105 | −37.67 |
| 8105828 | CCNB1 | NM_031966 | −5.85 | | | | |
| 8134257 | GNG11 | NM_004126 | −5.86 | | | | |
| 8168146 | KIF4A | NM_012310 | −5.91 | | | | |
| 7924096 | NEK2 | NM_002497 | −5.96 | | | | |
| 7901010 | KIF2C | NM_006845 | −5.99 | | | | |
| 7982358 | ARHGAP11A | NM_014783 | −6.05 | | | | |
| 8061579 | TPX2 | NM_012112 | −6.06 | | | | |
| 8124527 | HIST1H1B | NM_005322 | −6.09 | | | | |
| 8104234 | TRIP13 | NM_004237 | −6.12 | | | | |
| 8019857 | NDC80 | NM_006101 | −6.21 | | | | |
| 8054479 | MALL | NM_005434 | −6.22 | | | | |
| 7957260 | GLIPR1 | NM_006851 | −6.28 | | | | |
| 7970513 | C13orf3 | NM_145061 | −6.36 | | | | |
| 8118890 | SCUBE3 | NM_152753 | −6.44 | | | | |
| 8145570 | ESCO2 | NM_001017420 | −6.52 | | | | |
| 8008784 | PRR11 | NM_018304 | −6.58 | | | | |
| 7982663 | BUB1B | NM_001211 | −6.59 | | | | |
| 8139488 | IGFBP3 | NM_001013398 | −6.78 | | | | |
| 7900699 | CDC20 | NM_001255 | −6.82 | | | | |
| 8061564 | ID1 | NM_181353 | −6.96 | | | | |
| 7960340 | FOXM1 | NM_202002 | −7.07 | | | | |
| 8021635 | SERPINB2 | NM_002575 | −7.16 | | | | |
| 8084880 | HES1 | NM_005524 | −7.23 | | | | |
| 7953218 | RAD51AP1 | NM_006479 | −7.28 | | | | |
| 7929258 | KIF11 | NM_004523 | −7.43 | | | | |
| 8141016 | TFPI2 | NM_006528 | −7.44 | | | | |
| 8054702 | CKAP2L | NM_152515 | −7.45 | | | | |
| 8040223 | RRM2 | NM_001034 | −7.45 | | | | |
| 8102643 | CCNA2 | NM_001237 | −7.51 | | | | |
| 7991406 | PRC1 | NM_003981 | −7.53 | | | | |
| 8085138 | — | ENST00000355170 | −7.97 | | | | |
| 8124388 | HIST1H3B | NM_003537 | −8.03 | | | | |
| 7909568 | DTL | NM_016448 | −8.15 | | | | |
| 8014974 | TOP2A | NM_001067 | −8.18 | | | | |
| 7927710 | CDC2 | NM_001786 | −8.24 | | | | |
| 8054580 | BUB1 | NM_004336 | −8.37 | | | | |
| 7929334 | CEP55 | NM_018131 | −8.6 | | | | |
| 7937020 | MKI67 | NM_002417 | −8.95 | | | | |
| 7982757 | CASC5 | NM_170589 | −9.05 | | | | |
| 7974404 | CDKN3 | NM_005192 | −9.19 | | | | |
| 7994109 | PLK1 | NM_005030 | −9.5 | | | | |

TABLE 4-continued

Gene expression profiles of differentiated v. undifferentiated cell types.*

| Hepatic vs. Undifferentiated cells | | | | Neurogenic vs. Undifferentiated cells | | | |
| --- | --- | --- | --- | --- | --- | --- | --- |
| Probe Set ID | Gene Symbol | mRNA Accession | Fold change in expression | Probe Set ID | Gene Symbol | mRNA Accession | Fold change in expression |
| 8056572 | SPC25 | NM_020675 | −9.52 | | | | |
| 8094278 | NCAPG | NM_022346 | −9.8 | | | | |
| 7914878 | — | AY605064 | −10 | | | | |
| 8120838 | TTK | NM_003318 | −10.4 | | | | |
| 7916898 | DEPDC1 | NM_017779 | −10.7 | | | | |
| 7983969 | CCNB2 | NM_004701 | −10.9 | | | | |
| 7923086 | ASPM | NM_018136 | −12.1 | | | | |
| 8108301 | KIF20A | NM_005733 | −12.2 | | | | |
| 7989647 | KIAA0101 | NM_014736 | −12.4 | | | | |
| 8132318 | ANLN | NM_018685 | −13.1 | | | | |
| 8149955 | PBK | NM_018492 | −13.6 | | | | |
| 8001133 | SHCBP1 | NM_024745 | −14.1 | | | | |
| 8117594 | HIST1H2BM | NM_003521 | −14.5 | | | | |
| 7906930 | NUF2 | NM_145697 | −14.6 | | | | |
| 7979307 | DLG7 | NM_014750 | −18.7 | | | | |
| 8142981 | PODXL | NM_001018111 | −24.9 | | | | |
| 7951284 | MMP3 | NM_002422 | −60.1 | | | | |

*Additional information and data related to the genes listed in the Table are available in public domain and can be obtained from various publicly available databases including, GenBank, UniGene and RefSeq. Data obtained by using Affymetrix GENECHIP ® microarray technology.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method for selectively propagating CD117+ multipotent stem cells in a human skin explant, wherein the method comprises the steps of:
   (a) propagating cells of a human skin explant in a medium comprising amniotic fluid medium (AFM);
   (b) passaging the cells for at least 4 passages in the medium so that the CD117+ multipotent stem cells are obtained in the resulting cell culture;
   wherein the propagated CD117+ stem cells are capable of differentiation into cells of any of the three germ layers.

2. The method of claim 1, further comprising the step of determining the number of stem cells in the culture.

3. The method of claim 2, wherein the number of stem cells in the culture is determined after each passage.

4. The method of claim 2, wherein the number of stem cells in the culture is determined by determining the number of CD117+ stem cells in the culture.

5. The method of claim 1, wherein the cells are subject to at least 5, 6, 7, or 8 passages in the culture.

6. The method of claim 2, further comprising the step of prolonging the human skin explant culture by continued passages in the AFM until a desirable number of stem cells is obtained.

7. The method of claim 6, wherein the stem cell count reaches at least about 85%.

8. The method of claim 1, wherein the propagated stem cells are capable of differentiation into adipose, hepatic, muscle, or nerve cells under suitable conditions.

9. The method of claim 1, wherein the cells are cryopreserved after step (b).

* * * * *